United States Patent
D'Amore et al.

(10) Patent No.: US 12,077,885 B2
(45) Date of Patent: Sep. 3, 2024

(54) PROCESSING METHOD AND APPARATUS FOR MICRO-STRUCTURED ROPE-LIKE MATERIAL

(71) Applicants: University of Pittsburgh—Of the Commonwealth System of Higher Education, Pittsburgh, PA (US); Ri.MED Foundation, Palermo (IT)

(72) Inventors: Antonio D'Amore, Pittsburgh, PA (US); Daniel McKeel, Pittsburgh, PA (US); William R. Wagner, Gibsonia, PA (US)

(73) Assignees: University of Pittsburgh—Of the Commonwealth System of Higher Education, Pittsburgh, PA (US); Ri.MED Foundation (IT)

( * ) Notice: Subject to any disclaimer, the term of this patent is extended or adjusted under 35 U.S.C. 154(b) by 280 days.

(21) Appl. No.: 17/627,414

(22) PCT Filed: Jul. 15, 2020

(86) PCT No.: PCT/US2020/042115
§ 371 (c)(1),
(2) Date: Jan. 14, 2022

(87) PCT Pub. No.: WO2021/011639
PCT Pub. Date: Jan. 21, 2021

(65) Prior Publication Data
US 2022/0259773 A1    Aug. 18, 2022

Related U.S. Application Data

(60) Provisional application No. 62/937,497, filed on Nov. 19, 2019, provisional application No. 62/874,114, filed on Jul. 15, 2019.

(51) Int. Cl.
*D02G 3/26*    (2006.01)
*A61F 2/24*    (2006.01)
(Continued)

(52) U.S. Cl.
CPC ............. *D02G 3/26* (2013.01); *D01D 5/0076* (2013.01); *D02G 3/02* (2013.01); *D02G 3/36* (2013.01);
(Continued)

(58) Field of Classification Search
CPC .. D02G 3/02; D02G 3/26; D02G 3/36; D02G 3/448; D07B 1/02; D07B 3/00; D01D 5/0076
See application file for complete search history.

(56) References Cited

U.S. PATENT DOCUMENTS 1,975,504 A    10/1934  Formhals
5,216,115 A    6/1993   Kohn et al.
(Continued)

FOREIGN PATENT DOCUMENTS

WO    2012024390 A9    2/2012
WO    2012092138 A2    7/2012
(Continued)

OTHER PUBLICATIONS

Afifi et al., "Electrospinning of Continuous Aligning Yarns with a 'Funnel' Target", Molecular Materials and Engineering, 2010, pp. 660-665, vol. 295, Wiley InterScience, Weinheim.
(Continued)

*Primary Examiner* — Shaun R Hurley
(74) *Attorney, Agent, or Firm* — The Webb Law Firm

(57) ABSTRACT

Provided herein is an electrodeposition apparatus for producing long polymeric threads, yarns, or ropes. A method of preparing long polymeric threads, yarns or ropes also is provided.

17 Claims, 22 Drawing Sheets

(51) Int. Cl.
*D01D 5/00* (2006.01)
*D02G 3/02* (2006.01)
*D02G 3/36* (2006.01)
*D02G 3/44* (2006.01)
*D07B 1/02* (2006.01)
*D07B 3/00* (2006.01)

(52) U.S. Cl.
CPC ............... *D02G 3/448* (2013.01); *D07B 1/02* (2013.01); *D07B 3/00* (2013.01); *A61F 2/2457* (2013.01); *D07B 2201/104* (2013.01); *D07B 2201/2057* (2013.01); *D07B 2201/2066* (2013.01); *D07B 2201/2092* (2013.01); *D07B 2205/2039* (2013.01); *D07B 2205/2064* (2013.01); *D10B 2331/10* (2013.01); *D10B 2509/04* (2013.01)

(56) References Cited

U.S. PATENT DOCUMENTS

| | | | |
|---|---|---|---|
| 5,641,502 | A | 6/1997 | Skalla et al. |
| 8,286,413 | B2* | 10/2012 | Atkinson ................ D02G 3/36 57/210 |
| 9,085,830 | B2* | 7/2015 | Mitchell ............. D01D 5/0092 |
| 9,271,822 | B2 | 3/2016 | Xu et al. |
| 9,642,694 | B2 | 5/2017 | Hoerr et al. |
| 10,017,868 | B2 | 7/2018 | Akkus et al. |
| 10,137,223 | B2 | 11/2018 | Francis et al. |
| 2008/0260831 | A1 | 10/2008 | Badylak et al. |
| 2010/0148404 | A1* | 6/2010 | Smida ...................... D02G 3/36 425/66 |
| 2011/0082545 | A1 | 4/2011 | Freund |
| 2013/0337101 | A1 | 12/2013 | McGrath et al. |
| 2014/0322515 | A1 | 10/2014 | Parker et al. |
| 2016/0325013 | A1* | 11/2016 | Li ............................ A61P 21/00 |
| 2018/0044819 | A1* | 2/2018 | Inoue ....................... D02G 3/36 |
| 2018/0183107 | A1 | 6/2018 | Zhamu et al. |
| 2018/0223451 | A1 | 8/2018 | King et al. |
| 2018/0369848 | A1 | 12/2018 | Urban et al. |
| 2020/0010979 | A1* | 1/2020 | D'Amore ............ D01D 5/0076 |

FOREIGN PATENT DOCUMENTS

| | | |
|---|---|---|
| WO | 2016138416 A1 | 9/2016 |
| WO | 2018175234 A1 | 9/2018 |

OTHER PUBLICATIONS

Ali et al., "Direct electrospinning of highly twisted, continuous nanofiber yarns", The Journal of The Textile Institute, Jan. 2012, pp. 80-88, vol. 103 No. 1, Taylor and Francis, London.

Chang et al., "Fabrication of Microropes via Bi-electrospinning with a Rotating Needle Collector", Macromolecular Rapid Communications, 2010, pp. 2151-2154, vol. 31, WILEY-VCH Verlag Gmbh & Co. KGaA, Weinheim.

Chen et al., "A microstructurally inspired constitutive model for skin mechanics", Biomechanics and Modeling in Mechanobiology, 2020, pp. 275-289, vol. 19, Springer-Verlag GmbH, Germany.

Dalton et al., "Electrospinning with dual collection rings", Polymer, 2005, pp. 611-614, vol. 46, Elsevier Ltd.

D'Amore et al., "Characterization of the Complete Fiber Network Topology of Planar Fibrous Tissues and Scaffolds", Biomaterials, Jul. 2010, pp. 5345-5354, vol. 31 No. 20, Elsevier.

D'Amore et al., "Bi-layered polyurethane—Extracellular matrix cardiac patch improves ischemic ventricular wall remodeling in a rat model", Biomaterials, 2016, pp. 1-14, vol. 107, Elsevier.

D'Amore et al., "Nitro-Oleic Acid (NO2-OA) Release Enhances Regional Angiogenesis in a Rat Abdominal Wall Defect Model", Tissue Engineering Part A, 2018, pp. 889-904, vol. 24, Nos. 11 and 12, Termis.

Englen et al., "Granulocyte/macrophage colony-stimulating factor is expressed and secreted in cultures of murine 929 cells", Journal of Immunological Methods, 1995, pp. 281-283, vol. 184, Elsevier Science B.V.

Forward et al., "Free surface electrospinning from a wire electrode", 2012, pp. 492-503, vol. 183, Elsevier B.V.

Gong et al., "Novel Polyimide Materials Produced by Electrospinning", High Performance Polymers-Polyimides Based-From Chemistry to Applications, 2012, pp. 127-144 Intech.

Guan et al., "Biodegradable poly(ether ester urethane)urea elastomers based on poly(ether ester) triblock copolymers and putrescine: synthesis, characterization and cytocompatability", Biomaterials, 2004, pp. 85-96, vol. 25, Elsevier Ltd.

Ko et al., "Electrospinning of Continuous Carbon Nanotube-Filled Nanofiber Yarns", Advanced Materials, 2003, pp. 1161-1165, vol. 15 No. 14, WILEY-VCH Verlag Gmbh & Co. KGaA, Weinheim.

Liu et al., "One-step electrospun nanofiber-based composite ropes", Applied Physics Letters, 2007, pp. 083108-1-083108-3, vol. 90, American Institute of Physics.

Liu et al., "Preparation of short submicron-fiber yarn by an annular collector through electrospinning", Materials Letters, 2008, pp. 4467-4469, vol. 62, Elsevier B.V.

Lotus et al., "Electrospinning Route For the Fabrication of p-n Junction Using Nanofiber Yarns", Journal of Applied Physics, 2009, pp. 014303-1-014303-4, vol. 106, American Institute of Physics.

"Surgical polyglycolic acid suture reel" LotusMed, 2016, pp. 1-7, Nanjing Lotus International Trading Co., Ltd.

Mokhtari et al., "Advances in electrospinning: The production and application of nanofibres and nanofibrous structures", Textile Progress, 2016, pp. 119-219, vol. 48, No. 3, Taylor & Francis.

Molina et al., "Comparison of the host macrophage response to synthetic and biologic surgical meshes used for ventral hernia repair", Journal of Immunology and Regenerative Medicine, 2019, pp. 13-25, vol. 3, Elsevier.

Mondal et al., "Electrospun Self-Assembled Nanofiber Yarns", Journal of Applied Polymer Science, 2008, pp. 603-607, vol. 110, Wiley Periodicals, Inc.

Pan et al., "Continuous aligned polymer fibers produced by a modified electrospinning method", Polymer, 2006, pp. 4901-4904, vol. 47, Elsevier Ltd.

Shang et al., "Studies of Biaxial Mechanical Properties and Nonlinear Finite Element Modeling of Skin", MCB, 2009, pp. 93-104, vol. 7, No. 2, Tech Science Press.

Shuakat, "Electrospinning of Nanofibre Yarns Using Rotating Ring Collector", Deakin University, Aug. 20, 2014, pp. 1-202, Deakin University Australia Worldly.

Shuakat et al., "Recent Developments in Electrospinning of Nanofiber Yarns", Journal of Nanoscience and Nanotechnology, 2014, pp. 1389-1408, vol. 14, American Scientific Publishers.

Sicari et al., "The promotion of a constructive macrophage phenotype by solubilized extracellular matrix", Biomaterials, 2014, pp. 8605-8612, vol. 35, Elsevier Ltd.

Smit et al., "Continuous yarns from electrospun fibers", Polymer, 2005, pp. 2419-2423, vol. 46, Elsevier Ltd.

Stankus et al., "Hybrid nanofibrous scaffolds from electrospinning of a synthetic biodegradable elastomer and urinary bladder matrix", J Biomater Sci Polym Ed., 2008, pp. 635-652, vol. 19 No. 5, National Institute of Health.

Tan et al., "Robot-aided electrospinning toward intelligent biomedical engineering", Robotics and Biomimetics, 2017, pp. 1-13, vol. 4:17, Springer Open.

Teo et al., "Electrospun fibre bundle made of aligned nanofibres over two fixed points", Nanotechnology, 2005, pp. 1878-1884, vol. 16, Institute of Physics Publishing.

Teo et al., "A dynamic liquid support system for continuous electrospun yarn fabrication", Polymer, 2007, pp. 3400-3405, vol. 48, Elsevier Ltd.

Zhang et al., "Continuous micro-scaled rope engineering using a rotating multi-nozzle electrospinning emitter", Applied Physics Letters, 2016, pp. 151903-1-151903-5, vol. 106, AIP Publishing.

* cited by examiner $\omega_1 \ll \omega_2$ $\omega_1 < \omega_2$ $\omega_1 = \omega_2$ $\omega_1 > \omega_2$ $\omega_1 \gg \omega_2$

US 12,077,885 B2

PROCESSING METHOD AND APPARATUS FOR MICRO-STRUCTURED ROPE-LIKE MATERIAL

CROSS REFERENCE TO RELATED APPLICATIONS

This application is the United States national phase of International Application No. PCT/US2020/042115 filed Jul. 15. 2020, and claims the benefit of U.S. Provisional Patent Application No. 62/874,114 filed Jul. 15, 2019, and U.S. Provisional Patent Application No. 62/937,497 filed Nov. 19, 2019, the disclosure of each of which is incorporated herein by reference in its entirety.

Provided herein is a method of making a micro-structured rope-like material. Also provided is an apparatus for making a micro-structured rope-like material.

Rope-like materials, such as yarns, are useful for a number of biomedical applications, such as suture material, engineered tendon, engineered nerve, engineered ligament, and engineered chordae tendineae. Nanofibers produced from electrospinning have a naturally formed porous structure with excellent pore interconnectivity and the pores are in the range between tens of nanometers to a few micrometers. The open pore structure and high permeability to gas, along with the high surface area make them ideal porous membranes. Spools of a rope-like material, or yarns, with uniform cross-section cannot be readily made using existing methods. There is a substantial need for efficient and precise methods of manufacturing uniform electrospun ropes from electrospun fibers that permit precise control of fiber orientation.

SUMMARY

In one aspect or embodiment, an apparatus for producing a fibrous thread or rope is provided. The apparatus comprises:
  a base comprising an electric lead;
  a first rotating head rotatably connected to the base and electrically-connected to the electric lead of the base, wherein the first rotating head rotates about an axis of rotation, the first rotating head comprising:
    a first fiber collection spool;
    a motor configured to rotate the first fiber collection spool;
    a first electrode having a distal end and a proximal end attached to the first fiber collection spool and electrically-connected to the electric lead; and
    a first guide at the axis of rotation of the first rotating head configured to rotatably-retain the first electrode and through which the distal end of the first electrode is extended or extendable on action, e.g. rotation, of the first fiber collection spool;
  a second electrode having a distal end spaced apart from the distal end of the first electrode when the first electrode extends through the first guide and defining a gap between the first electrode and the second electrode, and connected at its proximal end to the electric lead or to a second electric lead; and a motor configured to rotate the first rotating head about the axis of rotation of the first rotating head.

According to another aspect or embodiment, a method of making a continuous fiber strand or rope is provided. The method comprises:
  initiating electrodeposition by feeding a polymer solution through an electrospray nozzle into a gap between a first electrode and a second electrode of an apparatus comprising:
    a base comprising an electric lead electrically-connected to a power source providing a voltage suitable for electrodeposition;
    a first rotating head rotatably connected to the base and electrically-connected to the electric lead of the base, wherein the first rotating head rotates about an axis of rotation, the first rotating head comprising:
      a first fiber collection spool;
      a motor configured to rotate the first fiber collection spool;
      a first electrode having a distal end and a proximal end attached to the first fiber collection spool and electrically-connected to the electric lead; and
      a first guide at the axis of rotation of the first rotating head configured to rotatably-retain the first electrode and through which the distal end of the first electrode is extended or extendable on action, e.g. rotation, of the first fiber collection spool, and wherein the distal end of the first electrode extends through the first guide;
    a second electrode having a distal end spaced apart from the distal end of the first electrode and defining a gap between the first electrode and the second electrode, and connected at its proximal end to the electric lead or to a second electric lead connected to a power source providing a voltage;
    a motor configured to rotate the first rotating head about the axis of rotation; and
    an electrospinning nozzle configured to deposit a polymer composition in the gap between the first electrode and the second electrode and electrically-connected to an electric lead and a power source providing a voltage to the electrospinning nozzle that produces an electrical field with the first and second electrode for electrodeposition of the polymer composition in the gap between the distal ends of the first electrode and second electrode,
  thereby forming nascent fiber or rope, and attaching the nascent fiber or rope to the first electrode and to the second electrode; and
  rotating the first fiber collection spool during electrodeposition of the polymer solution at a rate to first draw the first electrode, and then nascent electrodeposited thread or rope connected to the distal end of the first electrode, through the first guide and onto the first fiber collection spool, such that polymer fibers are electrodeposited onto and between nascent fiber or rope attached to the first electrode and the second electrode, thereby extending the length of the thread or rope and winding the nascent thread or rope about the first fiber collection spool.

A multilayer thread comprising a core layer of a polymer thread comprising aligned fibers having a first twist angle (e.g. degrees twist per cm), and a first layer of a polymer deposited over (e.g., directly over) at least a portion of the core layer, comprising aligned fibers having a second twist angle different from the first twist angle.

Non-limiting aspects or embodiments of the present invention will now be described in the following numbered clauses:

Clause 1: An apparatus for producing a fibrous thread or rope, comprising: a base comprising an electric lead;

a first rotating head rotatably connected to the base and electrically-connected to the electric lead of the base, wherein the first rotating head rotates about an axis of rotation, the first rotating head comprising:
  a first fiber collection spool;
  a motor configured to rotate the first fiber collection spool;
  a first electrode having a distal end and a proximal end attached to the first fiber collection spool and electrically-connected to the electric lead; and
  a first guide at the axis of rotation of the first rotating head configured to rotatably-retain the first electrode and through which the distal end of the first electrode is extended or extendable on action, e.g., rotation, of the first fiber collection spool;
a second electrode having a distal end spaced apart from the distal end of the first electrode when the first electrode extends through the first guide and defining a gap between the first electrode and the second electrode, and connected at its proximal end to the electric lead or to a second electric lead; and a motor configured to rotate the first rotating head about the axis of rotation of the first rotating head.

Clause 2: The apparatus of clause 1, wherein the distal end of the second electrode is spaced from 1 to 10 inches from the distal end of the first electrode when the first electrode extends through the first guide.

Clause 3: The apparatus of clauses 1 or 2, wherein the first electrode and/or second electrode are wire electrodes.

Clause 4: The apparatus of any one of clauses 1 to 3, further comprising: a second rotating head rotatably connected to the base and electrically-connected either to the electric lead of the base or to a second electric lead, wherein the second rotatable head rotates about an axis of rotation, the second rotating head comprising:
  a second fiber collection spool with a motor configured to rotate the second fiber collection spool;
  the second electrode having its proximal end attached to the second fiber collection spool; and
  a second guide at the axis of rotation of the second rotating head configured to rotatably-retain the second electrode and through which the distal end of the second electrode is extended or extendable on action, e.g., rotation, of the second fiber collection spool; and
a motor configured to rotate the second rotating head about the axis of rotation of the second rotating head.

Clause 5: The apparatus of any one of clauses 1-4, further comprising an electrospinning nozzle configured to deposit a polymer composition in the gap between the first electrode and the second electrode and connected to an electric lead,
  wherein the electrospinning nozzle is mounted on a movable stage,
  wherein the electrospinning nozzle is fluidly connected to a polymer reservoir to feed polymer through the electrospinning nozzle, and
  wherein a power source is connected to the electric lead of the electrospinning nozzle.

Clause 6: The apparatus of clause 5, further comprising an electrospray nozzle configured to deposit a liquid composition in the gap between the first electrode and the second electrode and connected to an electric lead,
  wherein the electrospray nozzle is mounted on a moveable stage,
  wherein the electrospray nozzle is fluidly connected to a liquid reservoir to feed liquid through the electrospinning nozzle, and
  wherein a power source is connected to the electric lead of the electrospray nozzle.

Clause 7: The apparatus of any one of clauses 1 to 6, further comprising one or more controllers adapted to control the direction and velocity of the motors of the first rotating head and the first fiber collection spool, and when present the motors of the second rotating head and the second fiber collection spool, thereby controlling direction and velocity of rotation of the first rotating head and the first fiber collection spool, and when present, the direction and velocity of rotation of the second rotating head and the second fiber collection spool.

Clause 8: The apparatus of clause 7, wherein the controller, or one or more additional controllers, controls, when present, location of the electrospinning nozzle, flow rate of the polymer solution through the electrospinning nozzle, location of the electrospray nozzle, flow rate of the liquid through the electrospray nozzle, charge on the first and second electrodes, charge on the electrospinning nozzle, and/or charge on the electrospray nozzle.

Clause 9: A method of making a continuous fiber strand or rope, comprising: initiating electrodeposition by feeding a polymer solution through an electrospray nozzle into a gap between a first electrode and a second electrode of an apparatus comprising:
  a base comprising an electric lead electrically-connected to a power source providing a voltage suitable for electrodeposition;
  a first rotating head rotatably connected to the base and electrically-connected to the electric lead of the base, wherein the first rotating head rotates about an axis of rotation, the first rotating head comprising:
    a first fiber collection spool;
    a motor configured to rotate the first fiber collection spool;
    a first electrode having a distal end and a proximal end attached to the first fiber collection spool and electrically-connected to the electric lead; and
    a first guide at the axis of rotation of the first rotating head configured to rotatably-retain the first electrode and through which the distal end of the first electrode is extended or extendable on action, e.g. rotation, of the first fiber collection spool, and wherein the distal end of the first electrode extends through the first guide;
  a second electrode having a distal end spaced apart from the distal end of the first electrode and defining a gap between the first electrode and the second electrode, and connected at its proximal end to the electric lead or to a second electric lead connected to a power source providing a voltage;
  a motor configured to rotate the first rotating head about the axis of rotation; and
  an electrospinning nozzle configured to deposit a polymer composition in the gap between the first electrode and the second electrode and electrically-connected to an electric lead and a power source providing a voltage to the electrospinning nozzle that produces an electrical field with the first and second electrode for electrodeposition of the polymer composition in the gap between the distal ends of the first electrode and second electrode, thereby forming nascent fiber or rope, and attaching the nascent fiber or rope to the first electrode and to the second electrode; and rotating the first fiber collection spool during electrodeposition of the polymer solution at a rate to first draw the first electrode, and then the nascent electrodeposited thread or rope connected to the distal end of the first electrode, through the first guide and onto the first fiber collection spool, such that polymer fibers are electrodeposited onto and between nascent fiber or rope attached to the first electrode and the second electrode, thereby extending the length of the thread or rope and winding the nascent fiber or rope about the first fiber collection spool.

Clause 10: The method of clause 9, further comprising electrospraying a liquid onto the fiber from an electrospray nozzle configured to deposit a liquid composition in the gap between the first electrode and the second electrode and connected to an electric lead and a power source providing a voltage suitable for electrospraying.

Clause 11: The method of clauses 9 or 10, wherein the apparatus further comprises: a second rotating head rotatably connected to the base and electrically-connected either to the electric lead of the base or to a second electric lead connected to a power supply providing a voltage suitable for electrodeposition, wherein the second rotatable head rotates about an axis of rotation, the second rotating head comprising:
  a second fiber collection spool with a motor configured to rotate the second fiber collection spool;
  the second electrode having a proximal end electrically connected to the electric lead of the base or to a second lead connected to a power supply and electrically-connected to the electric lead, and a distal end; and
  a second guide at the axis of rotation of the second rotating head configured to rotatably-retain the second electrode and through which the distal end of the second electrode is extended or extendable on rotation of the second fiber collection spool, and wherein the distal end of the first electrode extends through the second guide at least during initiation of electrodeposition; and
  a motor configured to rotate the second rotating head about the axis of rotation of the second rotating head.

Clause 12: The method of clause 11, further comprising, after rotating the first fiber collection spool during electrodeposition of the polymer solution, rotating the second fiber collection spool to draw the fiber away from the first fiber collection spool and through the second guide while electrodepositing an additional layer or a liquid on the fiber thread or rope.

Clause 13: The method of any one of clauses 9 to 12, comprising rotating at least the first head to impart a twist in the thread or rope and/or in one or more additional layers.

Clause 14: The method of any one of clauses 11 to 13, comprising rotating the first head and the second head synchronously to produce an untwisted thread or rope and/or an untwisted additional layer.

Clause 15: A thread or rope prepared according to the method of any one of clauses 9 to 14.

Clause 16: A multi-layer thread comprising a core layer of a polymer thread comprising aligned fibers having a first twist angle (e.g. degrees twist per cm), and a first layer of a polymer deposited over (e.g., directly over) at least a portion of the core layer, comprising aligned fibers having a second twist angle different from the first twist angle.

BRIEF DESCRIPTION OF THE DRAWINGS

FIG. 5A illustrates a twisting pattern with $\omega_1$ much less than $\omega_2$ ($\omega_1 << \omega_2$). FIG. 5B illustrates a twisting pattern with $\omega_1$ less than $\omega_2$ ($\omega_1 << \omega_2$). FIG. 5C illustrates a twisting pattern with $\omega_1$ is equal to $\omega_2$ ($\omega_1 = \omega_2$). FIG. 5D illustrates a twisting pattern with $\omega_1$ greater than $\omega_2$ ($\omega_1 > \omega 2$). FIG. 5E illustrates a twisting pattern with $\omega_1$ much greater than $\omega_2$ ($\omega_1 >> \omega_2$).

FIG. 6A depicts a rope 77.5 cm in length wrapped around the spool after a deposition time of 11 minutes Fabrication conditions were set as follows step 1 deposition time: 1 min, step 2 deposition time: 10 min, $V_P$: 10 kV, $V_G$: −5 kV, Flow rate: 10 ml/hr, Polymer gap: 5 cm, Electrodes gap: 5 cm, $\omega_1 = \omega_2$: 2 rpm, $v_{spool}$: minimum allowed but not quantified.

FIG. 6B is a scanning electron microscopy (SEM) image showing micro fibers aligned towards the longitudinal direction.

FIGS. 8A-8O: Representative SEM images of ropes formed with various configurations. FIG. 8A is an SEM of a rope formed with the $W_1 > \omega_2$ configuration depicted in FIG. 5D.

FIG. 9A shows the corresponding ultimate tensile stress in megapascals (MPa), FIG. 9B shows the corresponding initial modulus of elasticity in MPa, and FIG. 9C shows the percent strain at break for the ropes of FIGS. 8A, 8B, and 8C with statistically significant differences (*).

FIG. 11A is a photograph of an electrospun poly(ester urethane urea) layer (PEUU ES layer). FIG. 11B is a photograph of a cast poly(ester urethane urea) disc (PEUU cast). FIG. 11C is a photograph of an electrospun poly(ester urethane urea) wire (PEUU ES wire).

FIGS. 14A-140 depict the Western-Blot analysis of iNOS and Arginase expression. Bone marrow-derived macrophages were seeded on PEUU ES and cast 2 cm of diameter discs. After 7 days the samples were collected and lysed in RIPA buffer. Samples were charged in triplicates on the same gel. Western-blot membrane were incubated with anti β-actin, anti arginase1 and anti-iNOS (FIG. 14A). Immunoblotting was used to determine the quantitative results.

FIG. 14D shows the percentage of macrophages quantification of pro- and anti-inflammatory protein expression iNOS and Fizz normalized to the total nuclei number. One Way ANOVA statistical test shows statistically significant differences between means, *=p<0.05.

FIG. 15B depicts the collagen quantitative analysis, where the average collagen percentage under the 30-days sutured area was compared to normal skin collagen percentage. One Way ANOVA shows statistically significant differences among the groups, =p<0.05.

FIG. 16A shows the corresponding initial modulus of elasticity in MPa. The pre-implant suture initial modulus was compared to the rat skin initial modulus. Results of Brown-Forsythe and Welch ANOVA shown statistically significant differences between the pre implant PEUU cast wire, PPL, PGA and PDS groups versus the rat skin control group. Analysis showed no significant difference between PEUU ES and rat skin groups. FIG. 16B shows the corresponding percent strain at break. Results of Brown-Forsythe and Welch ANOVA shown statistically significant differences between the pre implant PEUU CAST and PEUU ES groups versus the rat skin control group. FIG. 16C shows the ultimate tensile strength in MPa. Results of Brown-Forsythe and Welch ANOVA shown statistically significant differences between the pre implant PPL, PGA and PDS groups versus the rat skin control group. Analysis showed no significant difference between PEUU cast and PEUU ES wire and rat skin groups.

DETAILED DESCRIPTION

Figure 1:
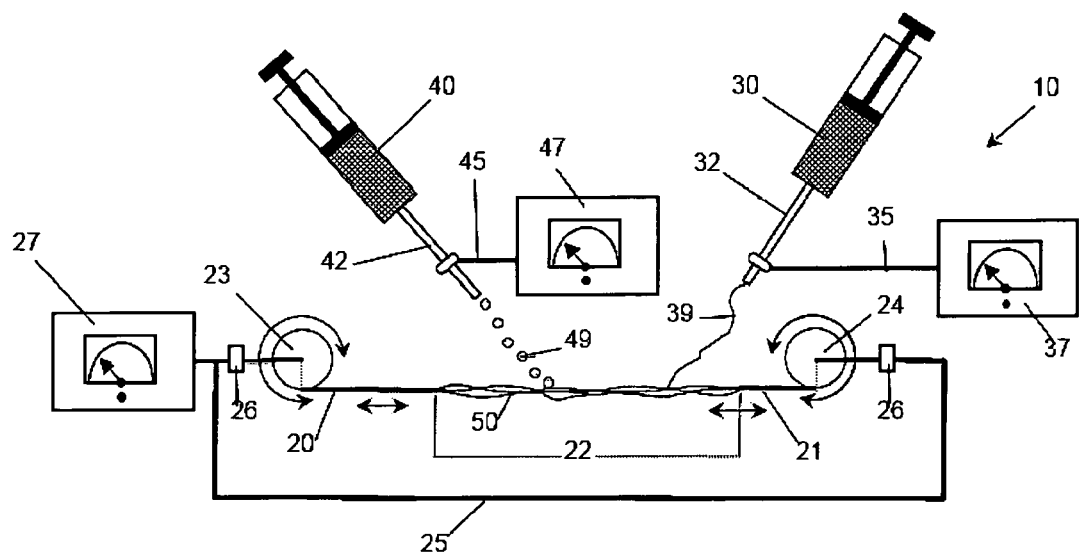
FIG. 1 depicts schematically aspects of an apparatus as described herein.

The use of numerical values in the various ranges specified in this application, unless expressly indicated otherwise, are stated as approximations as though the minimum and maximum values within the stated ranges are both preceded by the word "about." In this manner, slight variations above and below the stated ranges can be used to achieve substantially the same results as values within the ranges. Also, unless indicated otherwise, the disclosure of these ranges is intended as a continuous range including every value between the minimum and maximum values.

As used herein, the terms "comprising," "comprise" or "comprised," and variations thereof, are meant to be open ended. The terms "a" and "an" are intended to refer to one or more.

As used herein, the term "target" refers to points, surfaces or volumes in space influenced by the presence of an electrical charge or field to which polymer composition migrates and is deposited during the course of electrodeposition. In the context of the present disclosure, through use of two target electrodes, the target is the deposition axis produced by the two target electrodes.

The term "over", when describing deposition or layering of one layer over another does not require the layers to physically touch, such that one or more intervening layers may be deposited between the two layers. "Directly over" means two layers are in contact with each-other. A layer may include multiple sub-layers, e.g., of different compositional, structural, or physical qualities, and includes gradient layers, e.g., with differing compositional, structural, or physical qualities changing over the thickness of the layer.

As used herein, the "treatment" or "treating" of a wound or defect means administration to a patient by any suitable dosage regimen, procedure and/or administration route of a composition, device or structure with the object of achieving a desirable clinical/medical end-point, including attracting progenitor cells, healing a wound, correcting a defect, etc., for example repairing chordae tendineae.

A "prosthetic" article is a synthetic (artificial, or man-made) article that replaces an indicated body part, either temporarily or permanently, such as a chordae tendineae, a tendon, or a ligament. For example and without limitation, a prosthetic chordae tendineae is a synthetic chordae tendineae structure that either permanently or temporarily replaces, or otherwise stands in for, a natural chordae tendineae or a portion thereof. In aspects, if the prosthetic article degrades (bioerodes) over time, it includes, at least in part, a bioerodible portion that optionally may be replaced by nascent tissue over time, for example, by growth or differentiation of cells implanted within or on the article, or by growth or differentiation of cells that migrated into and/or onto the article, thereby forming nascent tissue, such as a nascent chordae tendineae.

As used herein, the term "patient" or "subject" refers to members of the animal kingdom including but not limited to human beings and "mammal" refers to all mammals, including, but not limited to human beings.

As used herein, the terms "cell" and "cells" refer to any types of cells from any animal, such as, without limitation, rat, mouse, monkey, and human. For example and without limitation, cells can be progenitor cells, e.g., pluripotent cells, including stem cells, induced pluripotent stem cells, multi-potent cells, or differentiated cells, such as endothelial cells and smooth muscle cells. In certain aspects, cells for medical procedures can be obtained from the patient for autologous procedures, or from other donors for allogeneic procedures. Methods of identifying, isolating and preparing cells, including stem cells and induced stem cells, are broadly-known.

A "cell growth scaffold" is a mesh, matrix, particle, surface, or other material upon which or into which a cell can be deposited and can be maintained in a living state, and often propagates (multiplies) in the presence of a cell growth medium.

A polymer composition is "biocompatible" in that the polymer composition and, where applicable, degradation products thereof, are substantially non-toxic to cells or organisms within acceptable tolerances, including substantially non-carcinogenic and substantially non-immunogenic, and are cleared or otherwise degraded in a biological system, such as an organism (patient) without substantial toxic effect. For biodegradable polymers, non-limiting examples of degradation mechanisms within a biological system include chemical reactions, hydrolysis reactions, and enzymatic cleavage.

As used herein, the term "polymer composition" is a composition comprising one or more polymers. As a class, "polymers" includes, without limitation, homopolymers, heteropolymers, co-polymers, block polymers, block co-polymers and can be both natural and synthetic. Homopolymers contain one type of building block, or monomer, whereas copolymers contain more than one type of monomer. The term "(co)polymer" and like terms refer to either homopolymers or copolymers.

A polymer "comprises" or is "derived from" a stated monomer if that monomer is incorporated into the polymer. Thus, the incorporated monomer that the polymer comprises is not the same as the monomer prior to incorporation into the polymer, in that at the very least, during incorporation of the monomer, certain groups, e.g., terminal groups, that are modified during polymerization are changed, removed, and/or relocated, and certain bonds may be added, removed, and/or modified. A monomer may be a "macromer", an oligomer or polymer that is the combination product of two or more smaller residues, and is employed as a monomer in preparation of a larger polymer. An incorporated monomer is referred to as a "residue" of that monomer.

A "moiety" is a portion of a molecule, compound or composition, and includes a residue or group of residues within a larger polymer.

A polymer is said to comprise a specific type of linkage if that linkage is present in the polymer, thus, a polyester comprises a plurality of ester linkages, a polyurethane comprises a plurality of urethane (e.g., carbamate) linkages, and a polyester urethane) urea comprises ester, urethane, and urea linkages. Unless otherwise specified, molecular weight for polymer compositions refers to weight average molecular weight ($M_w$). Composition of a copolymer may be expressed in terms of a ratio, typically a molar ratio, of incorporated monomers or as a feed ratio of monomers prior to polymerization. In the case of feed ratios, the relative amount of each monomer incorporated into the copolymer is influenced by reaction kinetics, and the nature of the chemical reaction(s) employed to join the monomers.

As described herein, a "fiber" is an elongated, slender, thread-like and/or filamentous structure. A "matrix" is any two- or three-dimensional arrangement of elements (e.g., fibers), either ordered (e.g., in a woven or non-woven mesh) or randomly-arranged (as is typical with a mat of fibers produced by traditional electrospinning) and can be isotropic or anisotropic. A "filament" is an article comprising one or more fibers.

The term "polymer" refers to both synthetic polymeric components and biological polymeric components. "Biological polymer(s)" are polymers that can be obtained from biological sources, such as, without limitation, mammalian or vertebrate tissue, as in the case of certain extracellular matrix-derived (ECM-derived) compositions, described herein. Biological polymers can be chemically modified by additional processing steps. Polymer(s), in general include, for example and without mono-polymer(s), copolymer(s), polymeric blend(s), block polymer(s), block copolymer(s), cross-linked polymer(s), non-cross-linked polymer(s), branched-, comb-, star-, and/or dendrite-shaped polymer(s), where polymer(s) can be formed into any useful form, for example and without limitation, a hydrogel, a porous mesh, a fiber, woven mesh, or non-woven mesh, such as, for example and without limitation, as a non-woven mesh formed by electrospinning.

By "biodegradable or "bioerodable", it is meant that a polymer, once implanted and placed in contact with bodily fluids and tissues, will degrade either partially or completely through chemical reactions with the bodily fluids and/or tissues, typically and often preferably over a time period of hours, days, weeks or months. Non-limiting examples of such chemical reactions include acid/base reactions, hydrolysis reactions, and enzymatic cleavage. The biodegradation rate of the polymer matrix may be manipulated, optimized or otherwise adjusted so that the matrix degrades over a useful time period. The polymer or polymers typically will be selected so that it degrades in situ over a time period to optimize mechanical conditioning of the tissue. For instance, in the case of chordae tendineae repair, it is desirable that the matrix dissolves over at least a week and preferably longer. More importantly, the matrix would have to retain its supportive capacity until tissue remodeling occurs, such as for at least 2-8 weeks, or longer. Biodegradable articles completely degrade in vivo within two years, and in many instances within one year.

As used herein, the term "derive" and any other word forms or cognates thereof, such as, without limitation, "derived" and "derives", refers to a component or components obtained from any stated source by any useful method.

Provided herein are methods and devices useful for preparing electrospun articles, for example and without limitation, threads, strings, sutures, ropes, prosthetic tendons, prosthetic ligaments, and the like. In aspects, the technology is useful broadly for preparation of fibers, such as suture material, and fiber-like tissue, including tendons and ligaments for orthopedic and dental applications, such as for chordae tendinae or periodontal ligaments, with fiber diameter being a linear function of the deposition time (e.g., 5 minutes of deposition produce fibers of 1.1 mm in diameter). While the methods and systems described herein are useful for engineering tissues, with use of biodegradable materials, they also can be utilized to form non-degradable materials or biomaterials, and materials other than tendons, or ligaments, or even for manufacture of non-implantable articles. While being particularly suited for preparation of articles useful for biomedical uses, such as tissue engineering (e.g., for production of engineered chordae tendineae), the articles prepare by the methods, devices, and systems described herein can be used for any purpose.

Therefore, provided herein are branched or unbranched filaments or polymeric articles, such as prosthetic tissues and filaments, useful, for example and without limitation, in medical procedures, such as heart and heart valve repair, or wound healing or repair. In one aspect, the filaments serve as a prosthetic tendon, such as chordae tendineae, which can be attached in place by any useful means, such as by suturing, stapling, or gluing, and optionally attached to other prosthetic articles, such as a prosthetic heart valve, for example, as described in International Patent Application Publication No. WO 2016/138416, incorporated herein by reference for its technical disclosure of prosthetic heart valves and methods of making prosthetic heart valves.

FIG. 1 depicts one aspect of a system 10 as described herein. As depicted in FIG. 1, system 10 includes a first electrode 20 and a second electrode 21 defining a gap 22 between the first and second electrode 20 and 21. In one aspect, the gap 22 between the first electrode 20 and the second electrode 21 is 2-10 cm, e.g., 5 cm. Electrodes 20 and 21 are electrically connected, via a lead 25, with rotatable electrical connectors 26, such as a slip ring, to a power supply 27. Alternatively, the first electrode 20 and the second electrode 21 are electrically connected to independent power supplies to further permit tailoring of the electrodeposition electrical field. Proximal ends (proximal in relation to the power supply or rotatable electrical connectors 26) of the first electrode 20 and the second electrode 21, are attached to a periphery of a first spool 23, and a second spool 24, respectively. Rotation of the spools 23, 24, as depicted by the curved arrows, results in movement of the electrodes toward or away from the spool, thereby extending or retracting the electrodes. Guides for the electrodes are not shown for clarity, but are described below. As shown by the dotted line, the electrodes 20, 21 are electrically-connected to the lead 25. The spools 23, 24 may be mounted with a rotatable electrical connector 26, such as a slip ring, to electrically-connect the electrode 20, 21 to the lead 25. The rotatable connectors 26, spools 23, 24, and electrodes 20, 21 are components of rotatable heads as described below, but which are not shown in FIG. 1 for clarity.

"Electrically-connected" means in electrical connection with a specified element such as an electric lead, and can be directly or indirectly electrically linked to the stated element. In the context of the first electrode or second electrode when mounted on a spool, the electrode(s) are electrically connected to an electric lead via intervening connectors, such as, for example and without limitation, rotatable electrical connectors, such as slip rings, connecting the head to the base 70, slip rings connecting the spool to the rotating head, and any wires, traces or other elements electrically-interconnecting the slip rings, electrode and electric lead of the base 70.

A spool is any structure or device that can draw, pull, and collect the fiber and can be any useful shape or configuration, and includes, but is not limited to a solid or gapped cylindrical structure.

The system 10 of FIG. 1 also includes a first syringe 30, comprising a first nozzle 32. A lead 35 is attached to the first nozzle 32, electrically connecting the first nozzle 32 to a second power supply 37. A polymer microfiber 39 is shown being electrodeposited (e.g., electrospun) from the first syringe 30 via the first nozzle 32. The system 10 also depicts an optional second syringe 40, comprising a second nozzle 42. A lead 45 is attached to the second nozzle 42, electrically connecting the nozzle 42 to a third power supply 47. Liquid droplets 49 are shown being electrodeposited (e.g., electrosprayed) from the second syringe 40 via the second nozzle 42 for wet deposition of the polymer microfibers 39 to form a fiber matrix 50. The polymer microfibers 39, and the liquid droplets 49 combine along an axis defined by the electrodes 20 and 21, to form the fiber matrix 50, as depicted. Liquids deposited by the second nozzle 42 for wet fabrication methods for depositing liquids, include, without limitation, saline, phosphate-buffered saline (PBS), cell media, blood products (e.g., serum, plasma, or platelet-rich plasma), cells, therapeutic compositions, solubilized ECM, or any other useful liquid to be deposited onto nascent electrospun polymer fibers or filaments. The system 10 does not necessarily include or require a second system for depositing a liquid and, therefore, only optionally includes the second syringe 40, the second nozzle 42, the lead 45, and the third power supply 47. The first, second, and optional third power supplies 27, 37, and 47, are independently controllable so that their output can be independently adjusted to permit optimization of electrodeposition of the components of the fiber matrix 50. The second syringe 40, comprising a second nozzle 42, lead 45, and second power supply 47, may also be used for electrodeposition of a second fiber-forming polymer as a second layer on the formed fiber.

The electrical and mechanical elements of the systems and methods described herein may be selected, combined, and/or optimized by a person of ordinary skill, and therefore can be represented in a large variety of physical and circuit structures. Leads as described herein are electrical conductors, and can comprise any suitable material and topological configuration for conducting an electric current, such as a wire or a conductive trace, or combinations of connectors. Further, electric circuit elements, such as, without limitation, leads or electrodes can comprise additional components, such as LEDs, switches, resistors, capacitors, diodes, transistors, integrated circuits (IC), or other electric or electronic elements, as are broadly-known in the art. Control circuits and devices can have any useful structure or topology and can comprise digital and/or analog control elements. Power supplies, controls, as well as other elements of the system may be housed individually, or all or some of the elements of the system can be housed together in an integrated housing or structure, as is within the skill of an electrical engineer with ordinary skill in the art.

Figure 2:
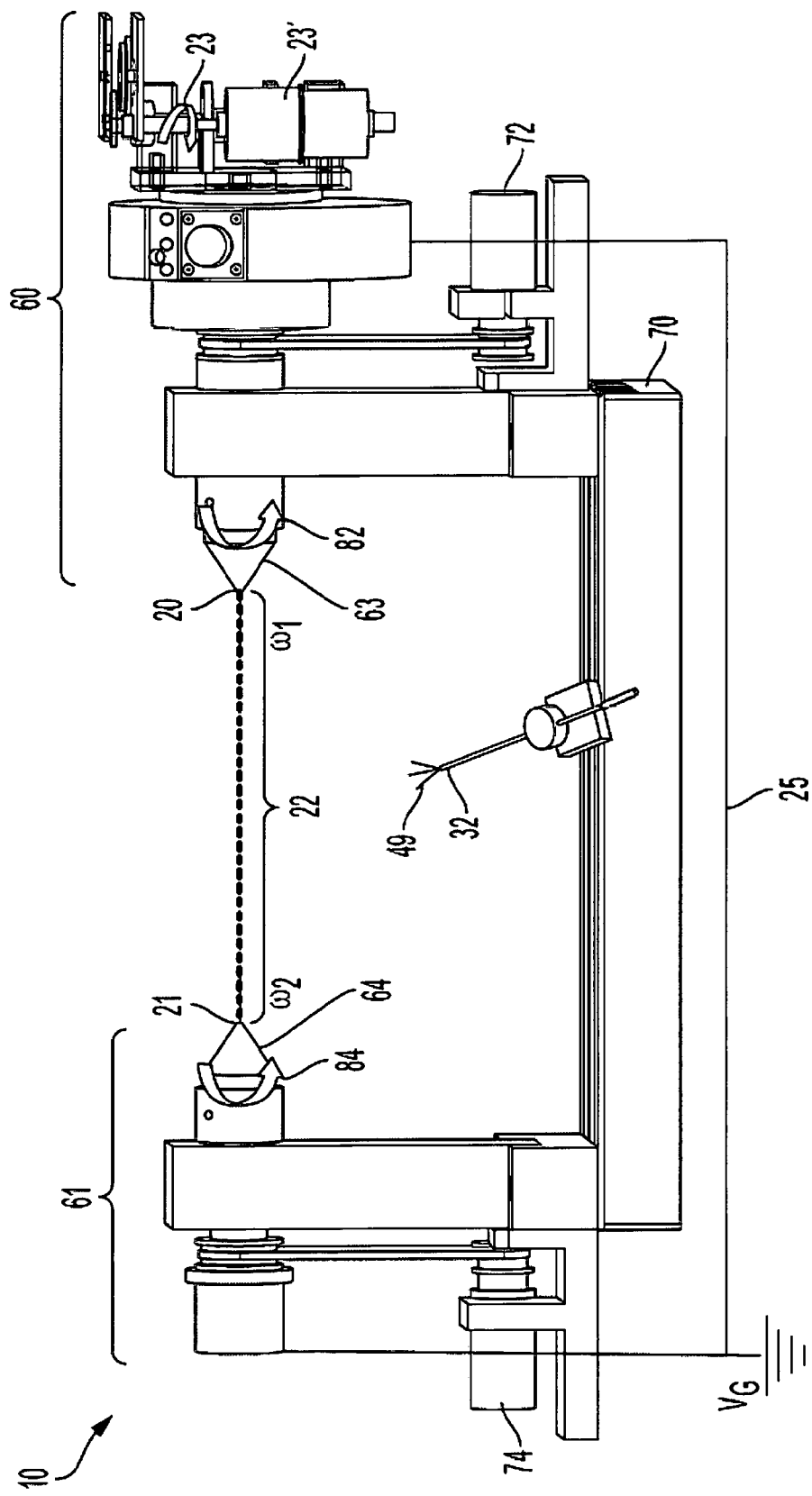
FIG. 2 depicts schematically aspects of an apparatus as described herein.

FIG. 2 depicts a second embodiment of the device 10. The device is essentially as depicted in FIG. 1, except the first head 60, including the first electrode 20 and the first spool 23, and second head 61, including the second electrode 21, are shown. Both the first head 60 and the second head 61 are rotatable about an axis of rotation (dotted line). Guides 63 and 64 are depicted. The guides 63, 64, having an aperture or channel through which the electrodes can extend, maintain the electrodes at the axis of rotation, and, as such, the electrodes are rotatably-retained by the guides when the distal end of the electrodes are extended through or pass through the guides. The guides may have any suitable shape, structure, or composition. As indicated by the arrows 82, 84 at guides 63 and 64, the first and second heads 60, 61 move independently about the axis of rotation.

Figure 3:
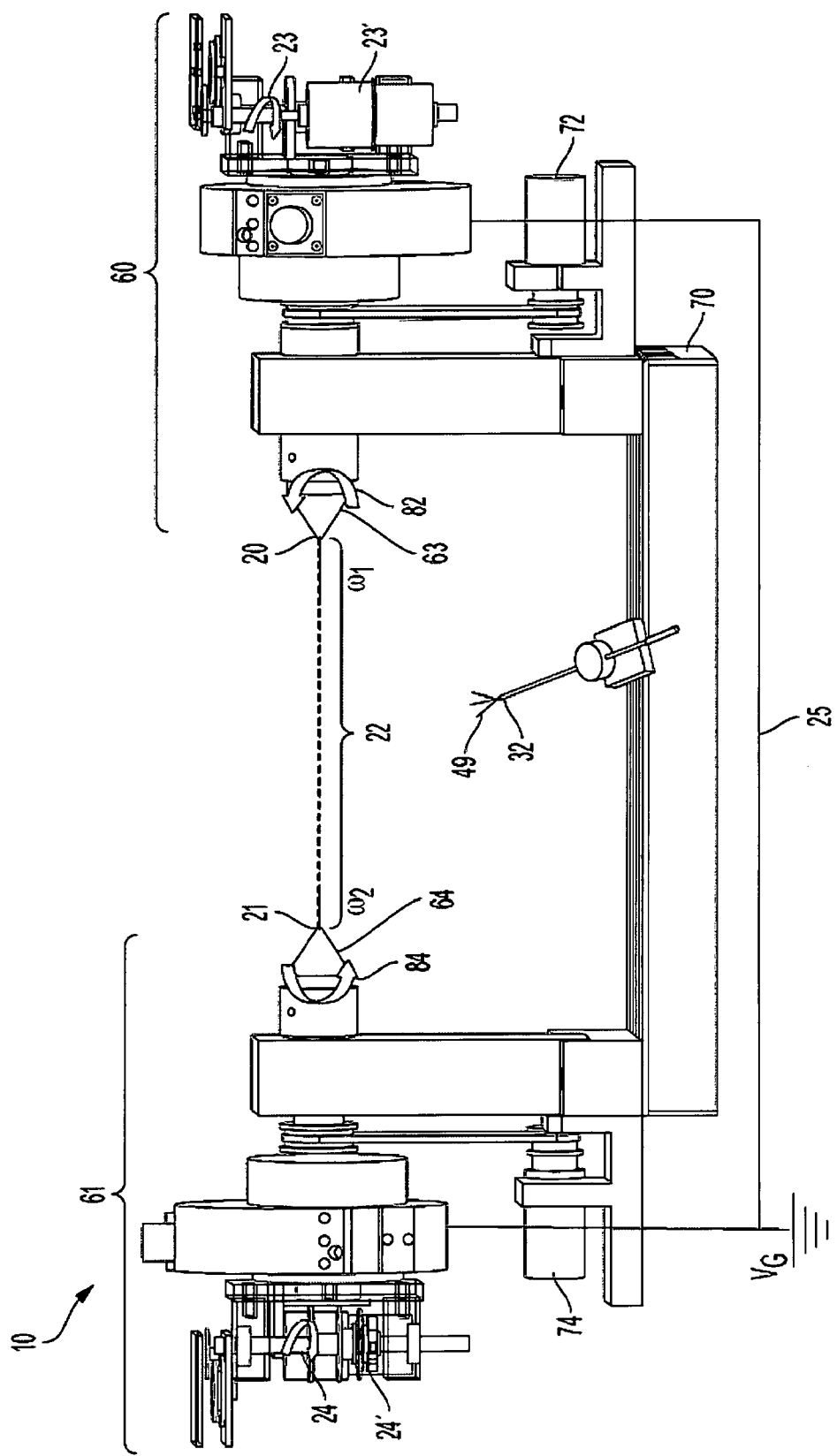
FIG. 3 depicts schematically aspects of an apparatus as described herein.
Figure 4:
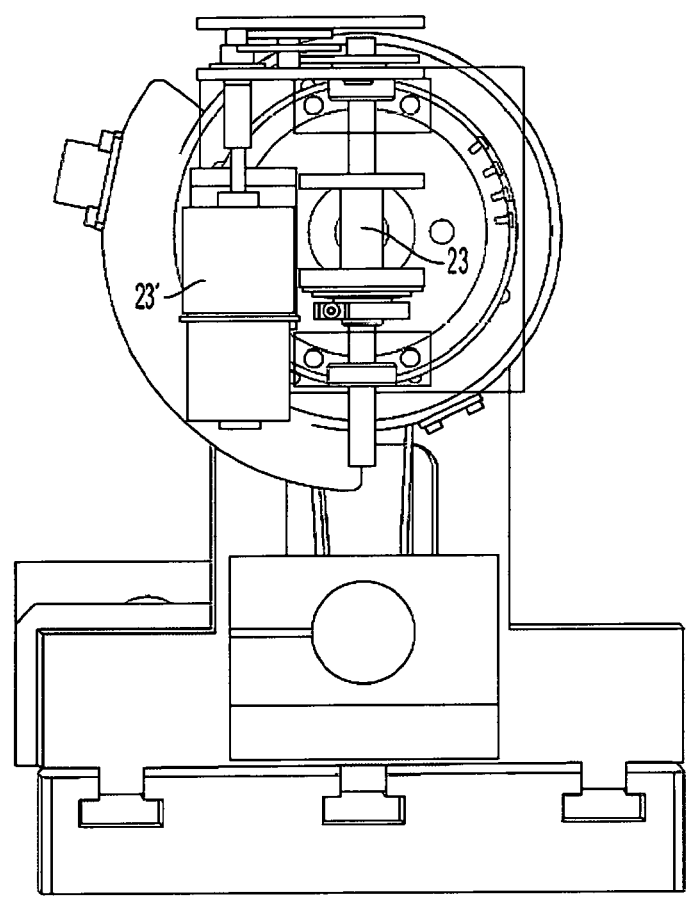
FIG. 4 is a side view of the device of FIG. 3, showing the configuration of the spool and spool motor.

FIG. 3 depicts an embodiment of the apparatus of FIG. 1, with spools 23, 24 and spool motors 23', 24' in both the first head 60 and the second head 61. Spool 23 and spool motor 23' are depicted in FIG. 4.

The spool motor 23' in FIG. 2 is positioned in the first head 60 and allows for processing the rope several times with alternating linear motion along the first motor 72 to second motor 74 axes. Two high voltage generators 27, 37 control the negative voltage of the two electrodes ($V_G$) and the voltage of the polymer ($V_P$). Slits on the base 70 and a moving arm are utilized to set the electrodes 20, 21 and polymer gaps. The gap 22 sets the original length of the rope when the spool motion is not activated. The first motor 72 in the first head 60 controls the rotation ($\omega_1$) of the first electrode 20, the second motor 74 in the second head 61 controls the rotation ($\omega_2$) of the second electrode 21, where the two electrodes 20, 21 spin around a common axis. The spool motor 23', housed in the first head 60, rotates around an axis perpendicular to the plane of the device schematic and controls the spool speed ($v_{spool}$). This mechanism is responsible for the collection of the produced rope. A polymer spinneret (not pictured) is positioned between the two electrodes 20, 21 distanced from the longitudinal axis of the electrode rotation and supplied with the positive voltage $V_P$. A Harvard apparatus (not shown) controls the polymer flow rate. At regimen, the polymer mass introduced in the system via electrospinning is equal to the polymer mass accumulated on the spool 23, which allows for the continuous production of the micro-fiber based rope.

In use, omitting the second syringe 40, comprising a second nozzle 42, lead 45, and second power supply 47 for simplicity of description. A charge is placed on the first and second electrodes 20, 21, and a suitable charge is placed on the nozzle 32, to promote electrodeposition of a polymer fiber in the gap 22. Initially, polymer material 39 is ejected into the gap 22, until a physical connection is made between the fibers and electrode 20. At that point, or after further electrodeposition to form a fiber of sufficient thickness, the first spool 23 is rotated (clockwise with respect to the view shown in FIG. 1) to pull, retract, and wrap the first electrode around the spool 23. By doing so, nascent (newly-formed) thread is pulled toward the first spool, and is collected about the spool by wrapping around the spool with the first electrode. The nascent fiber acts as an electrode, thereby maintaining the desired electrodeposition electric field. The second spool 24 is held immobile at this time. If the fiber to be produced is a single layer fiber, then the second spool 24 and its rotatable electrical connector 26 is not necessary, requiring any suitable electrode structure mounted in a fixed position.

Among other variables, the rate of electrodeposition of the polymer and rate of rotation of the spool 23 dictates the thickness of the nascent thread or rope. A thicker structure can be formed by slower rotation of the spool 23, and/or by increased deposition rate of the polymer.

Once deposition of the fiber is completed, the fiber is either completed, or it is run through the system 10 to add another layer either of the same polymer, a different polymer, or a liquid to the thread or rope. Electrodeposition of this second layer is accomplished by the same mechanism as electrodeposition of the first layer, except the fiber is moved in an opposite direction by rotating both spools 23, 24 to draw the fiber through the gap a second (or more) time. In relation to the view of FIG. 1, the spools 23, 24 are rotated in a counter-clockwise direction, thereby transferring the fiber through the gap 22 from the first spool 23 to the second spool 24. Additional material is electrodeposited on the fiber as it passes through the gap.

Figure 5A:
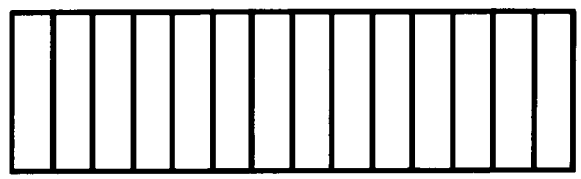
FIGS. 5A-5E illustrate schematically various twisting patterns that may be imparted on rotation of the heads of the device described herein.
Figure 5B:
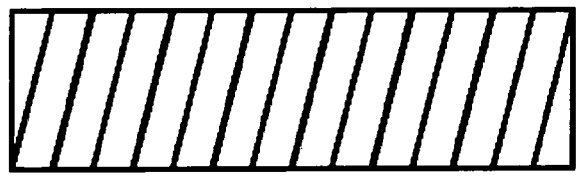
Figure 5C:
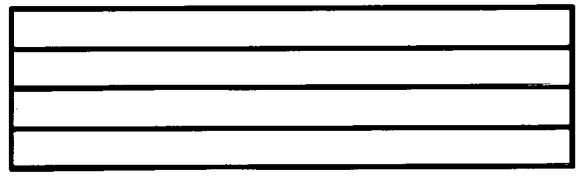
Figure 5D:
Figure 5E:
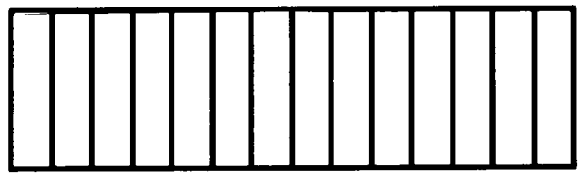

In embodiments, during electrodeposition of the fiber or of any additional layers on the fiber, one or both of the heads 60, 61 may be rotated independently about the rotational axis. FIGS. 5A-5E depict a principle for assembling fibers into layers with different orientations. The ratio between the rotational speed of the two electrodes dictates a different fiber arrangement, in particular if $\omega_1=\omega_2$: longitudinal (FIG. 5C), $\omega_1>>\omega_2$ or $\omega_1<<\omega_2$: circumferential (FIGS. 5A and 5E), $\omega_1>\omega_2$ or $\omega_1<\omega_2$: oblique (FIGS. 5B and 5D). Sequential depositions obtained under different electrode kinematics allow assembly of a thread or a rope with layers of different arrangement, for example, a longitudinally arranged core can be embedded into a circumferentially arranged jacket. Different materials can also be combined within the same construct. Thus, if the heads 60, 61 are rotated synchronously, that is at the same angular velocity, no twisting is imparted to the fiber, and if they are not synchronous, a twisting is imparted to the fiber or fiber layer.

The syringes 30 and 40 depicted, e.g., in FIG. 1 are used to deliver polymer (first syringe 30) and, optionally another liquid (second syringe 40). Second syringe 40 can be used to deliver a polymer composition different from the polymer of the first syringe 30. The nozzles are depicted in a specific orientation relating to the electrodes, but in practice can be placed in any suitable spatial location such as normal to the deposition axis extending between the two electrodes, and typically in an optimized spatial location. Although syringes, such as medical syringes, are depicted, any reservoir, nozzle, and fluid pumping apparatus can be employed, including peristaltic pumps, medical syringes, gravity-feed systems, etc. as are broadly-known. Likewise, nozzles can be any suitable size and shape conductor, including, without limitation, standard medical hypodermic needles, or metal tubes. Deposition and control of the rate of deposition of the polymer or other liquid can be manual, though for reproducibility and uniformity, deposition control is automated. For example, in one aspect, deposition is controlled by syringe pumps, such as programmable syringe pumps, as are broadly-known in the laboratory and medical arts. Control of deposition can be programmed into the syringe pump, or can be controlled by a separate computing unit or controller, such as a personal computer, workstation, smartphone, etc. Syringe and syringe pumps are one method of delivering controlled amounts of polymer and, where applicable, other liquids, in the described system. In another aspect, referring to the system 10 depicted in FIG. 1, rather than syringes 30 and 40, a peristaltic pump, or an infusion pump, is used to control delivery of the polymer and, where applicable, other liquids. Choice of an appropriate delivery mechanism for the polymer and, where applicable, other liquid(s), is well-within the abilities of a person of ordinary skill in the engineering arts. Further, additional sources of other polymers, or other constituents, such as ECM material, useful in preparation of a fiber matrix, may be added, and electrodeposited under suitable conditions.

As with the polymer reservoirs, such as syringes, control of the rotation of the heads 60 and 61, and spools 23, 24 may be automated and controlled by a suitable controller, such as a computing unit. A computing unit or controller can include a processor, computer-readable instructions for the processor, storage media, memory, and any other useful elements found in computers, smart-devices, smartphones, and the like.

In further reference to FIG. 1, and equally applicable to other systems described herein, the parameters, such as voltage, distance between a pair of target electrodes, distance between nozzles, distance between nozzles and an axis between tips of the electrodes, etc., are exemplary and are provided for illustrative purposes. The power supplies can be individual as shown (e.g., referring to the system depicted in FIG. 1, 10 kV for the first power supply 27, −5 kV for the second power supply 37, and 8 kV for the third power supply 47), or integrated into a single housing.

In use, one or more, or all, of the nozzles and electrodes are spatially positioned using a manual or automatic positioning system, such as X-Y or X-Y-Z stages, or other robotics, as are broadly-known. The nozzles and electrodes may be positioned statically during the entire electrospinning process, or may be moved relative to each other or rotated during the process, for example, to ensure uniform deposition over the entire electrospun article, or to produce thicker, thinner, or in a broader sense, different, regions in the electrospun article.

The electrodes (target electrodes) can be prepared from any suitable conductive material, such as aluminum, copper, steel, iron, silver, gold, platinum, carbon/graphite, titanium, etc., and any alloy or composite structure, such as brass or bronze, that can serve as an electrode. The target electrodes have a tip that can be pointed, rounded, flat or have any suitable shape—so long as it has a small, e.g., less than 5 mm, 4 mm, 3 mm, 2 mm, or 1 mm diameter, such as its largest diameter normal to the deposition axis (extending between opposing electrode tips). Thus, the electrode typically is cylindrical or tapers to the tip. In one aspect, the electrodes are flexible, permitting winding about a spool, such as a wire electrode, which is a flexible electrode having a high aspect ratio, such as a wire or thin metal rod, and in the context of the present invention, can be withdrawn onto a spool, e.g., wrapped around a spool with formed thread or rope. The electrode may have a needle tip at its distal end, such as a flat tip, a conical tip, or a frustoconical tip. In aspects, portions of the electrode optionally are covered with an insulator, such as the guide described above. The distal tip of the electrode may have a diameter of less than 1 mm.

Electrodeposition, e.g., electrospinning, is used to deposit the polymer composition and, optionally, the ECM gel and/or other liquid, gel, cell, or other biological or therapeutic constituents, such as a mammalian blood product, media buffer solution, medium, drug products, antibodies, etc. In its simplest sense, electrodeposition is caused by the deposit of a liquid composition, such as polymer fibers in the case of electrospinning, onto a target surface in the case of a single electrode and/or to a deposition axis or space created by and between spatially-distanced electrodes. Electrospinning methods are well-known in the field of tissue engineering and are conducted essentially as described below. Electrospinning permits fabrication of structures that resemble the scale and fibrous nature of the native extracellular matrix (ECM). The ECM is composed of fibers, pores, and other surface features at the sub-micron and nanometer size scale. Such features directly impact cellular interactions with synthetic materials such as migration and orientation. Electrospinning also permits fabrication of oriented fibers to result in structures with inherent anisotropy, or structures having varying anisotropy at different parts of the structure. These aligned structures can influence cellular growth, morphology and ECM production.

The process of electrospinning involves placing a polymer-containing fluid (for example, a polymer solution, a polymer suspension, or a polymer melt) in a reservoir equipped with a small orifice, such as a needle, pipette tip, metal tube, or other metal structure referred to herein as a nozzle and also can be referred to as a spinneret, and a metering pump, such as a syringe pump or a peristaltic pump. One electrode of a high voltage source is placed in electrical contact with the polymer-containing fluid or orifice, while another electrode is placed in electrical contact with a target (traditionally, typically a collector screen or rotating mandrel), and in the context of the present invention, two spaced-apart electrodes that produce a target deposition axis in the space between the two electrodes, or even multiple spaced-apart electrodes that produce a target deposition space in the space between the electrodes in a pattern dictated by the relative position of the electrodes and electrical field produced by the electrodes.

During electrospinning, the polymer-containing fluid is charged by the application of high voltage to the solution or orifice (for example, about 3-15 kV) and then forced through the small orifice by the metering pump that provides steady flow. While the polymer-containing fluid at the orifice normally would have a hemispherical shape due to surface tension, the application of the high voltage causes the otherwise hemispherically-shaped polymer-containing fluid at the orifice to elongate to form a conical shape known as a Taylor cone. With sufficiently high voltage applied to the polymer-containing fluid and/or orifice, the repulsive electrostatic force of the charged polymer-containing fluid overcomes the surface tension and a charged jet of fluid is ejected from the tip of the Taylor cone and accelerated towards the target, target deposition axis or target deposition space, which typically is biased (electrically-charged) so that the total voltage difference between the nozzle and the target is sufficiently large to cause effective electrodeposition, e.g., 20 kV, though other potentials and polarities are able to achieve effective electrodeposition, for example, between −2 and −20 kV. Optionally, a focusing ring with an applied bias (for example, 1 to 10 kV) can be used to direct the trajectory of the charged jet of polymer-containing fluid. Under certain conditions, for instance with solutions lacking sufficient viscosity and/or electrospun with certain tolerances, a fiber is not formed, but a spray is formed, depositing discrete droplets onto the target instead of a fiber. This is electrospraying.

Relative charges of the nozzle and electrodes may be the reverse polarity (e.g., with the target, target deposition axis or target deposition space, which typically is biased (electrically charged) between 2 to 10 kV, and the nozzle being charged between from −3 to −15 kV). As the charged jet of fluid travels towards the biased target, target deposition axis or target deposition space, the solvent typically evaporates during mid-flight, leaving behind a polymer fiber on the biased target, at the target deposition axis, or within the target deposition space. If the fluid is a polymer melt, the molten polymer cools and solidifies in mid-flight and is collected as a polymer fiber on the biased target, at the target deposition axis, or within the target deposition space. As the polymer fibers accumulate on the biased target, at the target deposition axis, or within the target deposition space, a non-woven, porous mesh is formed.

The systems and devices described herein are described as mandrel-less, meaning they are configured to, or adapted to, produce an electrospun article in a gap or space defined by two, three, or more, spaced-apart target electrodes, and not wholly onto a physical target surface, such as a rotating mandrel, as with conventional electrodeposition processes. The electrospun fibers of a mandrel-less system accumulate in the space between the spaced-apart target electrodes and span the gap between those electrodes, forming a fiber matrix attached to the electrodes and extending into a space between the electrodes, thereby connecting the electrodes.

The properties of the electrospun structures, e.g., elastomeric scaffolds, can be tailored by varying the electrospinning conditions. For example, when the biased target, target deposition axis, or target deposition space is relatively close to the orifice, the resulting electrospun mesh tends to contain unevenly thick fibers, such that some areas of the fiber have a "bead-like" appearance. However, as the biased target, target deposition axis, or target deposition space is moved further away from the orifice, the fibers of the non-woven mesh tend to be more uniform in thickness. Moreover, the biased target, target deposition axis, or target deposition space can be moved relative to the orifice to create different qualities of the article depending on the relative locations of the nozzle and the target, target deposition axis or target deposition space.

In the context of the present invention, due to the electrical field created by two or more spaced-apart target electrodes, fibers of the non-woven mesh are oriented (therefore, anisotropic) towards the direction of the axis of deposition between the tips of the electrodes. In this instance, the resulting non-woven mesh filament may have a higher resistance to strain in the direction parallel to the fibers, compared to the direction perpendicular to the fibers making the resultant article particularly suited for use as prosthetic tendons, ligaments, or as filaments in general. The properties of the electrospun structure may also be varied by changing the magnitude of the voltages applied to the electrospinning system. In one exemplary and non-limiting aspect, the electrospinning apparatus includes a nozzle biased to 12 kV, target electrodes biased to −7 kV each, and one or more optional nozzles biased to 3-10 kV to allow for concurrent electrospinning of different polymer compositions, or electrospray of cell solutions, ECM material, liquids, liquids comprising therapeutic agent(s), blood products, etc. Examples of useful orifice diameters range from 0.1 to 2 mm (I.D.) and a useful target distances (distance from nozzle to axis of deposition) range from 1 to 17 cm. Other electrospinning conditions that can be varied include, for example and without limitation, the feed rate of the polymer solutions, the solution concentrations, the polymer molecular weight, the injectors—deposition target axis distance, as well as the nozzle—target axis relative positioning and trajectories, e.g., controlled via robotic control systems.

As indicated above, in certain examples, electrospinning is performed using two or more nozzles, wherein each nozzle is a source of a same or different polymer solution. The nozzles may be biased (electrically charged) with different biases or the same bias in order to tailor the physical and chemical properties of the resulting fiber matrix.

When the electrospinning is to be performed using a polymer suspension, the concentration of the polymeric component in the suspension can also be varied to modify the physical properties of the elastomeric scaffold. For example, when the polymeric component is present at relatively low concentration, the resulting fibers of the electrospun non-woven mesh have a smaller diameter than when the polymeric component is present at relatively high concentration. Without wishing to be limited by theory, it is believed that lower concentration solutions have a lower viscosity, leading to faster flow through the orifice to produce thinner fibers. One skilled in the art can adjust polymer concentrations to obtain fibers of desired characteristics. Useful ranges of concentrations for the polymer component are from 1 wt % to 25 wt %, 4 wt % to 20 wt %, and from 10 wt % to 15 wt %, including increments therebetween for all ranges.

In one non-limiting example, the structure is produced by co-electrospinning a polymer suspension comprising a synthetic polymeric component and a biological polymeric component, along with electrospraying an ECM gel and/or other liquid(s). In another non-limiting example, the polymeric component of the structure is produced by electrospinning a polymer suspension comprising a synthetic polymeric component from one nozzle and a polymer suspension comprising a biological polymeric component from another nozzle. Non-limiting examples of useful range of high-voltage to be applied to the polymer suspension is from 0.5 to 30 kV, from 5 to 25 kV, and from 10 to 15 kV.

If present, an ECM gel component of the structure is sprayed (e.g., pressure sprayed) or electrosprayed concurrently with the electrospinning of the polymer(s). Likewise, the liquid component of the wet-electrospun layer(s) is sprayed or electrosprayed concurrently with the polymeric constituents.

The articles described herein are prepared from any natural or synthetic biocompatible, electrodepositable material. In certain illustrative examples below, the filaments are prepared from a urethane, for example, and without limitation, a poly(ester-urethane)urea (PEUU), which is synthesized using putrescine as a chain extender and two-step solvent synthesis method described. PEUU features include high elasticity and mechanical strength coupled with controllable biodegradative and cell-adhesive properties. The polymer composition has found use in a number of in vivo scenarios including as a cardiac patch, in prosthetic heart valves, in abdominal wall repair, and in vascular grafts. Alternative chemistries allow the polyurethanes to include added non-thrombogenic chemical moieties, and to use non-degradable polyurethanes as permanent structures not meant to be remodeled in situ. Additional biodegradable polymeric compositions are known in the art, and exhibit suitable strength and elasticity for use along with, or substituting for the described PEUU.

In aspects, focusing on biomedical usage, polymeric components suitable for the articles described herein are any polymer that is biocompatible and optionally is biodegradable. In certain non-limiting examples, the biodegradable polymers may comprise homopolymers, copolymers, and/or polymeric blends comprising, without limitation, one or more of the following monomers: glycolide, lactide, caprolactone, dioxanone, and trimethylene carbonate. In other non-limiting examples, the polymer(s) comprise labile chemical moieties, non-limiting examples of which include esters, anhydrides, polyanhydrides, or amides, which can be useful in, for example and without limitation, controlling the degradation rate of the scaffold and/or the release rate of therapeutic agents from the scaffold, where applicable. Alternatively, the polymer(s) may contain polypeptides or biomacromolecules as building blocks which are susceptible to chemical reactions once placed in situ. In one non-limiting example, the polymer composition comprises a polypeptide comprising the amino acid sequence alanine-alanine-lysine, which confers enzymatic lability to the polymer. In another non-limiting example, the polymer composition comprises a biomacromolecular component derived from an ECM. For example, the polymer composition may comprise collagen so that collagenase, which is present in situ, can degrade the collagen. The polymers used herein may be elastomeric, meaning they change shape on application of a deforming force and substantially return to an original shape when the deforming force is removed.

In another non-limiting example, the synthetic polymeric component comprises any hydrolytically, chemically, biochemically, and/or proteolytically labile group, non-limiting examples of which include an ester moiety, amide moiety, anhydride moiety, specific peptide sequences, and generic peptide sequences.

In certain aspects, degradable polymers used to make the articles described herein also release therapeutic agents when they are implanted in and degrade within the patient's body. For example, the individual building blocks of the polymers may be chosen such that the building blocks themselves provide a therapeutic benefit when released in situ through the degradation process. In one example, one of the polymer building blocks is putrescine, which has been implicated as a substance that causes cell growth and cell differentiation. In another aspect, therapeutic agents may be linked using any applicable chemistry, to the polymer composition so that it is released upon degradation of the polymer composition in situ, such as by a linker comprising an ester bond or another biodegradable linkage.

In certain aspects, the biodegradable polymers comprise homopolymers, copolymers, and/or polymeric blends comprising, without limitation, one or more of the following monomers: glycolide, lactide, caprolactone, dioxanone, and trimethylene carbonate. In other aspects, the polymer(s) comprise labile chemical moieties, non-limiting examples of which include esters and anhydrides, which can be useful in, for example and without limitation, controlling the degradation rate of the articles described herein.

Non-limiting examples of a bioerodible polymer useful for tissue growth scaffolds, hydrogels, or particles include: a polyacrylate or polymethacrylate, a polyacrylamide or polymethacrylamide, a polyester, a polyester-containing copolymer, a polyanhydride, a polyanhydride-containing copolymer, a polyorthoester, and a polyorthoester-containing copolymer. In one aspect, the polyester or polyester-containing copolymer is a poly(lactic-co-glycolic) acid (PLGA) copolymer. In other aspects, the bioerodible polymer is selected from the group consisting of poly(lactic acid) (PLA); poly(trimethylene carbonate) (PTMC); poly(caprolactone) (PCL); poly(glycolic acid) (PGA); poly(glycolide-co-trimethylenecarbonate) (PGTMC); poly(L-lactide-co-glycolide) (PLGA); polyethylene-glycol (PEG-) containing block copolymers; and polyphosphazenes. Additional bioerodible, biocompatible polymers include: a poly(ester urethane) urea (PEUU); poly(ether ester urethane)urea (PEEUU); poly(ester carbonate)urethane urea (PECUU); poly(carbonate)urethane urea (PCUU); a polyurethane; a polyester; a polymer comprising monomers derived from alpha-hydroxy acids such as: polylactide, poly(lactide-co-glycolide), poly(L-lactide-co-caprolactone), polyglycolic acid, poly(D,L-lactide-co-glycolide), and/or poly(L-lactide-co-D,L-lactide); a polymer comprising monomers derived from esters including polyhydroxybutyrate, polyhydroxyvalerate, polydioxanone, and/or polyglactin; a polymer comprising monomers derived from lactones including polycaprolactone; or a polymer comprising monomers derived from carbonates including polycarbonate, polyglyconate, poly(glycolide-co-trimethylene carbonate), or poly(glycolide-co-trimethylene carbonate-co-dioxanone).

Non-limiting examples of natural bioerodible polymers useful for preparation of tissue growth scaffolds, hydrogels, or particles include proteins, glycosaminoglycans, and polysaccharides, such as, without limitation, cross-linked or non-cross-linked: heparin, alginate (alginic acid), guar gum, carboxymethylcellulose (CMC), hyaluronic acid, pullulan, carrageenan, pectin, acid modified chitosan, xanthan gum, agarose, chitosan, collagen, elastin, cellulose, hyaluronic acid, and gelatin, and a mixture of any of the foregoing. Synthetic and/or natural polymer compositions may be cross-linked by any of a large variety of known crosslinking methods, using any of the large variety of known cross-linkers, for example, gelatin and/or hyaluronan crosslinked with methacrylate to produce methacrylated gelatin and/or hyalyronan, e.g., by photocrosslinking.

Although bioerodible constituents may be preferred, non-bioerodible polymers may be used that either do not erode substantially in vivo or erode over a time period of greater than two years. Compositions such as, for example and without limitation, polytetrafluoroethylene (PTFE), poly(ethylene-co-vinyl acetate), poly(n-butylmethacrylate), poly(styrene-b-isobutylene-b-styrene), and polyethylene terephthalate are considered to be non-bioerodable polymers. Other suitable non-bioerodable polymer compositions are broadly known in the art, for example, in stent coating and transdermal reservoir technologies. The growth scaffolds described herein may comprise a non-erodible polymer composition.

For uses that do not involve tissue engineering or biocompatibility, virtually any polymer composition amenable to the electrospinning process can be used to prepare the filamentous articles, and branched filamentous articles described herein, and any particles, solutions, liquids, etc. may be co-electrodeposited with the filaments.

With respect to polymer synthesis, diamines, diols, and diisocyanates are useful building blocks for preparing certain of the polymer compositions described herein. Diamines as described above have the structure $H_2N$—R—$NH_2$ where "R" is an aliphatic or aromatic hydrocarbon or a hydrocarbon comprising aromatic and aliphatic regions. The hydrocarbon may be linear or branched. Examples of useful diamines are putrescine (R=butylene) and cadaverine (R=pentylene). Useful diols include polycaprolactone (e.g., Mw 1000-5000), multi-block copolymers, such as polycaprolactone-PEG copolymers, including polycaprolactone-b-polyethylene glycol-b-polycaprolactone triblock copolymers of varying sizes. Other building blocks for useful diols include, without limitation glycolides (e.g., polyglycolic acid (PGA)), lactides, dioxanones, and trimethylene carbonates. Diisocyanates have the general structure OCN—R—NCO, where "R" is, e.g., an aliphatic or aromatic hydrocarbon or a hydrocarbon comprising aromatic and aliphatic regions. The hydrocarbon may be linear or branched.

For the purpose of illustration, in aspects, the electrospun polymer composition comprises PEUU, PECUU, PCUU, and/or PECUU, which may be synthesized as follows. PEUU can be manufactured by reacting a diol with a diisocyanate to form a prepolymer and then reacting the prepolymer with a diamine. A non-limiting example of such a PEUU is an elastomeric polymer made from polycaprolactone diol ($M_w$ 2000) and 1,4-diisocyanatobutane, using a diamine chain extender such as putrescine. One non-limiting example or a method for preparing a PEUU polymer is a two-step polymerization process whereby polycaprolactone diol ($M_w$ 2000), 1,4-diisocyanatobutane, and diamine are combined in a 2:1:1 molar ratio. In the first step to form the prepolymer, a 15 wt % solution of 1,4-diisocyanatobutane in DMSO (dimethyl sulfoxide) is stirred continuously with a 25 wt % solution of polycaprolactone diol in DMSO. Then, stannous octoate is added and the mixture is allowed to react at 75° C. for 3 hours. In the second step, the prepolymer is reacted with a diamine to extend the chain and to form the polymer. In one example, the diamine is putrescine, which is added drop-wise while stirring and allowed to react at room temperature for 18 hours. In one example, the diamine is lysine ethyl ester, which is dissolved in DMSO with triethylamine, added to the prepolymer solution, and allowed to react at 75° C. for 18 hours. After the two step polymerization process, the polymer solution is precipitated in distilled water. Then, the wet polymer is immersed in isopropanol for three days to remove any unreacted monomers. Finally, the polymer is dried under vacuum at 50° C. for 24 hours.

PEEUU may be made by reacting polycaprolactone-b-polyethylene glycol-b-polycaprolactone triblock copolymers with 1,4-diisocyanatobutane and putrescine. In one non-limiting example, PEEUU is obtained by a two-step reaction using a 2:1:1 reactant stoichiometry of 1,4-diisocyanatobutane:triblock copolymer:putrescine. According to one non-limiting example, the triblock polymer can be prepared by reacting poly(ethylene glycol) and ε-caprolactone with stannous octoate ($Sn(Oct)_2$) at 120° C. for 24 hours under a nitrogen environment. The triblock copolymer is then washed with ethyl ether and hexane, then dried in a vacuum oven at 50° C. In the first step to form the prepolymer, a 15 wt % solution of 1,4-diisocyanatobutane in DMSO is stirred continuously with a 25 wt % solution of triblock copolymer in DMSO. Then, stannous octoate is added and the mixture is allowed to react at 75° C. for 3 hours. In the second step, putrescine is added drop-wise under stirring to the prepolymer solution and allowed to react at room temperature for 18 hours. The PEEUU polymer solution is then precipitated with distilled water. The wet polymer is immersed in isopropanol for 3 days to remove unreacted monomer and dried under vacuum at 50° C. for 24 hours.

PECUU may be synthesized using a blended soft segment of polycaprolactone (PCL) and poly(1,6-hexamethylene carbonate) (RHO) and a hard segment of 1,4-diisocyanatobutane (BDI) with chain extension by putrescine. Different molar ratios of PCL and PHC can be used to achieve different physical characteristics. Putrescine is used as a chain extender by a two-step solvent synthesis method. In one example, the (PCL+PHC):BDI:putrescine molar ratio is defined as 1:2:1. Variable molar ratios of PCL and RHO (e.g., PCL/PHC ratios of 100/0 (yielding a PEUU), 75/25, 50/50, 25/75 and 0/100 (yielding a PCUU)) are completely dissolved in DMSO in a 3-neck flask with argon protection and then BDI is added to the solution, following 4 drops of $Sn(Oct)_2$. The flask is placed in an oil bath at 70° C. After 3 h, the prepolymer solution is cooled at room temperature and then a putrescine/DMSO solution is added dropwise into the agitated solution. The final polymer solution concentration is controlled to be approximately 4% (w/v). Then the flask is placed in an oil bath and kept at 70° C. overnight. The polymer is precipitated in an excess volume of cool deionized water and then dried in a vacuum at 60° C. for 3 days. Polyurethane ureas synthesized from the different PCL/PHC molar ratios defined above are referred to as PEUU, PECUU 75/25, PECUU 50/50, PECUU 25/75, and PCUU, respectively. In practice, the yields of all final products using this method is approximately 95%.

In additional aspects, the polymer composition may include polyethylene terephthalate (PET, e.g., DACRON). Of note, PET is less biodegradable than the copolymers described above, and is stiffer. PET scaffolds structures are made essentially in the manner described herein for PEUU and other polymer compositions described herein. Polymer concentrations and infusion rates may be altered to accommodate the different qualities of the PET composition, for example and without limitation, for PET, 20% w/v in HFIP at 12 mL/h infusion rate, as used in the examples below.

In other examples, the polymer composition comprises a tyrosine polyarylate (TPA). As with PET, TPA is less biodegradable than the polyurethane copolymers described above, and also is stiffer. IPA scaffolds structures are made essentially in the manner described herein for PEUU and other polymer compositions. Polymer concentrations and infusion rates may be altered to accommodate the different qualities of the IPA composition, for example and without limitation, for IPA, 12% w/v in HFIP at 20 mL/h infusion rate. Tyrosine polyarylates are commonly prepared from an aliphatic acid and a tyrosine-derived diphenol. Non-limiting examples of useful aliphatic acids include: succinic acid, adipic acid, sebacic acid, and dicarboxylic acid chlorides or anhydrides. Non-limiting examples of tyrosine-derived diphenols include desaminotyrosyl-tyrosine alkyl esters, where the alkyl is, for example, one of ethyl, hexyl and octyl) (DTE). As an example, Poly(DTE-co-27.5 DT succinate) is used. TPAs and methods of making TPAs are described, for example, in U.S. Pat. No. 5,216,115 and United States Patent Application Publication No. 2011/0082545, each of which is incorporated herein by reference for its technical disclosure, disclose useful TPAs.

As used herein, the terms "extracellular matrix" and "ECM" refer to a natural composition useful for cell growth. ECM is decellularized or devitalized tissue, and is a complex mixture of structural and non-structural biomolecules, including, but not limited to, proteins, glycosaminoglycans, proteoglycans, antimicrobials, chemoattractants, cytokines, and growth factors, such as collagens, elastins, and laminins. In mammals, ECM often comprises about 90% collagen in its various forms. The composition and structure of ECMs vary depending on the source of the tissue. For example, small intestine submucosa (SIS), urinary bladder matrix (UBM), liver stroma ECM, and dermal ECM each differ in their overall structure and composition due to the unique cellular niche needed for each tissue.

Generally, any tissue source, and therefore any type of extracellular matrix (ECM) can be used to produce ECM products to be implanted with the cell sheet as described herein. ECM materials are prepared, for example, from decellularized or devitalized ECM material that, optionally, has not been dialyzed. ECM materials are broadly-known, and are commercially-available in many forms, and may be prepared from a natural ECM (tissue), or from an in vitro source wherein the ECM is produced by cultured cells and comprises one or more polymeric components (constituents) of native ECM. ECM can be engineered into a variety of three-dimensional structures. In aspects, ECM is isolated from a vertebrate animal, for example, from a warm blooded mammalian vertebrate including, but not limited to, human, monkey, pig, cow, horse, or sheep. The ECM may be derived from any organ or tissue, including without limitation, nerve tissue, connective tissue, urinary bladder, intestine, liver, heart, esophagus; spleen, cartilage; meniscus; bone, stomach, and dermis. Tissue for preparation of ECM as described herein may be harvested in any useful manner. The ECM can comprise any portion or tissue obtained from an organ, including, for example and without limitation, and where relevant, submucosa, epithelial basement membrane, tunica propria, etc. The ECM material may take many different forms, though in the context of chordae tendineae repair, is a sheet, tube, bundled fiber, cylinder, or chordae tendineae-shaped, and affixed in place at the site of implantation using, for example and without limitation, a medically acceptable adhesive or sutures.

ECM material may be decellularized, disinfected, sterilized, and/or dried by any useful method. The ECM material can be sterilized by any of a number of standard methods without loss of its ability to induce endogenous tissue growth. For example, the material can be sterilized by propylene oxide or ethylene oxide treatment, gamma irradiation treatment (0.05 to 4 mRad), gas plasma sterilization, peracetic acid sterilization, or electron beam treatment. The material can also be crosslinked by treatment with glutaraldehyde, but this treatment substantially alters the material such that it is slowly resorbed or not resorbed at all and incites a different type of host remodeling which more closely resembles scar tissue formation or encapsulation, rather than constructive remodeling. Cross-linking of the protein material can also be induced with carbodiimide or dehydrothermal or photooxidation methods. Often, ECM is disinfected by immersion in 0.1% (v/v) peracetic acid (σ), 4% (v/v) ethanol, and 96% (v/v) sterile water for 2 h. The decellularized tissue is then washed twice for 15 min with PBS (pH=7.4) and twice for 15 min with deionized water.

Commercially available ECM materials derived from small intestinal submucosa or SIS include, but are not limited to, Surgisis™, SurgisisES™, Stratasis™, and Stratasis-ES™ (Cook Urological Inc.; Indianapolis, Indiana) and GraftPatch™ (Organogenesis Inc.; Canton, Massachusetts). In another example, the ECM material is derived from dermis. Commercially available preparations include, but are not limited to Pelvicol™ (crosslinked porcine dermal collagen, sold as Permacol™ in Europe; Bard Medical Division, Covington, GA), Repliform™ (Microvasive; Boston, Massachusetts) and Alloderm™ (LifeCell; Branchburg, New Jersey). In another example, the ECM is derived from urinary bladder. Commercially available preparations include, but are not limited to UBM (Acell Corporation; Jessup, Maryland).

ECM gels can be made by any useful method. In its broadest sense, to produce an ECM gel according to one non-limiting example, ECM-derived scaffold materials, e.g., decellularized or devitalized tissue, are comminuted and solubilized to form a hydrogel. In one example, the solubilized hydrogel is not dialyzed. In aspects, solubilization may be achieved by digestion with a suitable acid protease, such as pepsin, under acidic conditions. In one non-limiting aspect, decellularized tissue is lyophilized, comminuted, and is then solubilized with an acid protease. In certain aspects, the decellularized tissue is not dialyzed and/or is not cross-linked (subjected to a cross-linking method) prior to digestion with the acid protease. The acid protease may be, without limitation, pepsin or trypsin, and in one example is pepsin. The decellularized tissue typically is solubilized at an acid pH suitable or optimal for the protease, for example, between pH 1.5 and 3, or in a 0.01 M HCl solution (pH~2). The solution typically is solubilized for 12-48 hours, depending upon the tissue type, with mixing (stirring, agitation, admixing, blending, rotating, tilting, etc.). Once the decellularized tissue is solubilized, the pH is raised to between 7.2 and 7.8, and according to one example, to pH 7.4. Bases, such as bases containing hydroxyl ions, including NaOH, can be used to raise the pH of the solution. Likewise buffers, such as an isotonic buffer, including, without limitation, Phosphate Buffered Saline (PBS), can be used to bring the solution to a target pH, or to aid in maintaining the pH and ionic strength of the gel to target levels, such as physiological pH and ionic conditions. The neutralized digest solution is gelled at temperatures approaching 37° C., typically at any temperature over 25° C., though gelation proceeds much more rapidly at temperatures over 30° C. and as the temperature approaches physiological temperature (37° C.). The method typically does not include a dialysis step prior to gelation, yielding a more-complete ECM-like matrix that typically gels at 37° C. more slowly than comparable collagen or dialyzed ECM preparations.

In one aspect, the filaments are prepared from a synthetic polymeric composition. In another, the polymeric composition combines a synthetic polymer with an ECM gel, such as described in International Patent Application Publication No. WO 2012/024390, or solutions comprising finely comminuted ECM particles, such as powdered ECM. Where the synthetic polymer and ECM gel are mixed, any ratio of biodegradable, elastomeric polymer to ECM gel that shows excellent cellular infiltration, while displaying adequate tensile strength and elasticity may be used, for example, a useful ratio of polymer to gel ranges from 70%-85%:15%-30%, including increments therebetween. This can be achieved, for example, by codepositing the biodegradable, elastomeric polymer by electrospinning, and the ECM gel by electrospraying, as described above, for example, in FIG. 1. See, e.g., United States Patent Application Publication No. 2008/0260831, incorporated herein by reference for its technical disclosure. (See also, Stankus et al., Hybrid nano-fibrous scaffolds from electrospinning of a synthetic biodegradable elastomer and urinary bladder matrix, *J Biomater. Sci. Polym. Ed.* (2008) 19(5):635-652.) In the Stankus article, PEUU was mixed with solubilized UBM ECM and was electrospun.

In aspects, the electrodeposited, fiber-forming polymer composition comprises a biomacromolecular component derived from an ECM, or the biomacromolecular component derived from an ECM is electrosprayed or otherwise electrodeposited with a separately-electrodeposited fiber-forming polymer composition. For example, the electrodeposited composition may comprise the biomacromolecule collagen so that collagenase, which is present in situ, can degrade the collagen. As an example, the polymer composition may comprise one or both of a collagen and an elastin. Collagen is a common ECM component and typically is degraded in vivo at a rate faster than many synthetic bioerodable polymers. Therefore, manipulation of collagen content in the polymer composition can be used as a method of modifying bioerosion rates in vivo. Collagen may be present in the polymer composition in any useful range, including, without limitation, from about 2% wt. to about 95% wt., for example, in the range of from about 25% wt. to about 75% wt., inclusive of all ranges and points therebetween, including from about 40% wt. to about 75% wt., including about 75% wt. and about 42.3% wt. Elastin may be incorporated into the polymer composition in order to provide increased elasticity. Elastin may be present in the polymer composition in any useful range, including without limitation, from about 2% wt. to about 50% wt., inclusive of all ranges and points therebetween, including from about 40% wt. and about 42.3% wt., inclusive of all integers and all points therebetween and equivalents thereof. In one non-limiting example, collagen and elastin are present in approximately equal amounts in the polymer composition. In another example, the sum of the collagen and elastin content in the polymer composition is in any useful range, including, without limitation, from about 2% wt. to about 95% wt., for example, in the range of from about 25% wt. to about 75% wt., inclusive of all ranges and points therebetween, including from about 40% wt. to about 75% wt., including about 75% wt. and about 42.3% wt.

As can be appreciated by those of ordinary skill in the art, multiple, different polymer compositions can be mixed together in a suitable solvent in one reservoir and concurrent electrodeposited from a single nozzle, and, therefore, as a single fiber. In another aspect, different polymer compositions are provided in different reservoirs, and are deposited independently from different nozzles concurrently, or at different times and rates. In one aspect, synthetic and biological polymer compositions are mixed in a suitable solvent and are electrodeposited concurrently in one stream from a single nozzle. In another aspect, the synthetic and biological polymer are electrodeposited independently from different reservoirs and nozzles.

In another example, at least one therapeutic agent is added to the article described herein before it is implanted in the patient or otherwise administered to the patient. Generally, the therapeutic agents include any substance that can be coated on, embedded into, absorbed into, adsorbed to, chemically linked to with a labile or digestible bond, or otherwise attached to or incorporated onto or into the structure or incorporated into a drug product that would provide a therapeutic benefit to a patient. Non-limiting examples of such therapeutic agents include antimicrobial agents, growth factors, emollients, retinoids, and topical steroids. Each therapeutic agent may be used alone or in combination with other therapeutic agents. For example and without limitation, a structure comprising neurotrophic agents or cells that express neurotrophic agents may be applied to a wound that is near a critical region of the central nervous system, such as the spine. Alternatively, the therapeutic agent may be blended with the polymer while a polymer is being processed. For example, the therapeutic agent may be dissolved in a solvent (e.g., DMSO) and added to the polymer blend during processing. In another example, the therapeutic agent is mixed with a carrier polymer (e.g., polylactic-glycolic acid microparticles) which is subsequently processed with an elastomeric polymer. By blending the therapeutic agent with a carrier polymer or elastomeric polymer itself, the rate of release of the therapeutic agent may be controlled by the rate of polymer degradation.

In certain aspects, the therapeutic agent is a growth factor, such as a neurotrophic or angiogenic factor, which optionally may be prepared using recombinant techniques. Non-limiting examples of growth factors include basic fibroblast growth factor (bFGF), acidic fibroblast growth factor (aFGF), vascular endothelial growth factor (VEGF), Human Vascular Endothelial Growth Factor-165 (hVEGF$_{165}$), Vascular endothelial growth factor A (VEGF-A), Vascular endothelial growth factor B (VEGF-B), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons. Commercial preparations of various growth factors, including neurotrophic and angiogenic factors, are available from R & D Systems, Minneapolis, Minnesota; Biovision, Inc, Mountain View, California; ProSpec-Tany TechnoGene Ltd., Rehovot, Israel; and Cell Sciences®, Canton, Massachusetts In certain aspects, the therapeutic agent is an antimicrobial agent, such as, without limitation, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate.

In certain aspects, the therapeutic agent is an anti-inflammatory agent, such as, without limitation, an NSAID, such as salicylic acid, indomethacin, sodium indomethacin trihydrate, salicylamide, naproxen, colchicine, fenoprofen, sulindac, diflunisal, diclofenac, indoprofen, sodium salicylamide; an anti-inflammatory cytokine; an anti-inflammatory protein; a steroidal anti-inflammatory agent; or an anti-clotting agents, such as heparin; nitro-fatty acids, such as nitro-oleic acid or nitro-conjugated linoleic acid. Other drugs that may promote wound healing and/or tissue regeneration may also be included.

In one aspect, articles described herein are prepared by electrospinning of a biodegradable, elastomeric polymer, and concurrent deposition of an ECM gel, a blood product, media, saline, an isotonic buffer, or any other suitable liquid or gel, by spraying, e.g., by physically spraying or by electrospraying. Other compounds or components may be incorporated into a structure as described herein by any method, including absorption, adsorption, mixing, etc. Blood products include, without limitation, blood, serum, plasma, platelet-rich plasma, and may be, for example, allogeneic or autologous, for example human for use in humans, or the blood product is prepared from blood of a patient into whom the article is to be implanted.

In aspects, the polymer matrix, as deposited or formed, is porous. As used herein, the term "porosity" refers to a ratio between a volume of all the pores within the electrodeposited polymer matrix and a volume of the whole electrodeposited polymer matrix. Pores may be filled with liquid, gel, and/or cells in wet-electrodeposited matrices. For instance, a polymer matrix with a porosity of 85% would have 85% of its volume containing pores and 15% of its volume containing the polymer. In certain non-limiting examples, the porosity of the structure is at least 60%, 65%, 70%, 75%, 80%, 85%, or 90%, or increments therebetween. In another non-limiting example, the average pore size of the structure is between 0.1 and 300 microns, 0.1 and 100 microns, 1-25 microns, including increments therebetween. For example and without limitation, a structure that acts as a barrier to bacteria and other pathogens may have an average pore size of less than 0.5 microns or less than 0.2 microns. Because the structures described herein are manufactured by electrospinning, it is often advantageous to adjust the pore size or degree of porosity by varying the polymer concentration of the electrospinning solution, by varying the spinning distance from the nozzle to the target deposition axis (the axis between the tips of the opposing target electrodes), the polymer Mw, the target—nozzle voltage gap, and/or any other factor that would alter porosity during the electrodeposition process. For example and without limitation, the average pore size may be increased by increasing the amount of polymeric components within the suspension used for electrospinning, which results in larger fiber diameters and, therefore, larger pore sizes. In another non-limiting example, the average pore size can be increased by increasing spinning distance from the nozzle to the target deposition axis, which results in less adherence between fibers and a looser matrix. Where ECM gel or a liquid is co-deposited during the electrospinning, many of the pores (that is, a large percentage of the pores or interstices) in the deposited polymer are filled with the ECM gel.

EXAMPLE 1

Figure 6A:
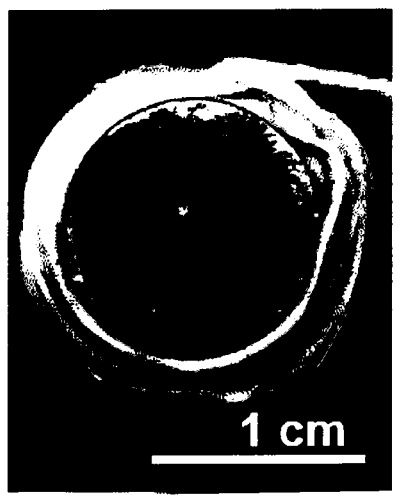
FIGS. 6A-6B: Example of fabricated micro-structured rope.
Figure 6B:
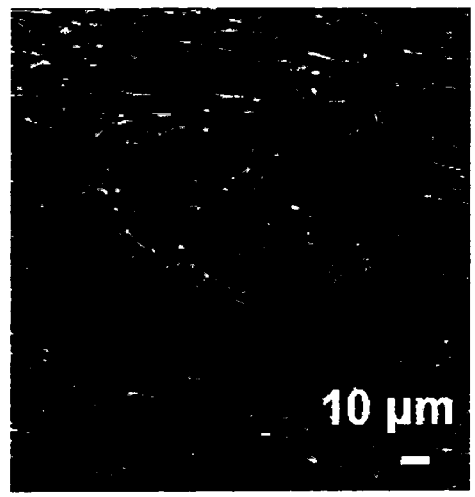
Figure 6C:
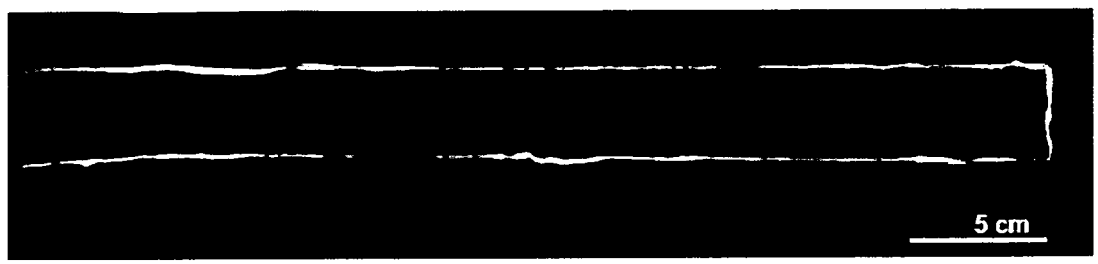
FIG. 6C depicts the unspooled 77.5 cm length rope.

A prototype of the apparatus described herein, essentially as shown in FIG. 2, was prepared. As shown in FIG. 6A thread of significant length was produced.

EXAMPLE 2

Additional testing has been conducted, demonstrating the ability to produce uniform, rope-like materials with varying twisting profiles using a device essentially as described herein.

Figure 7A:
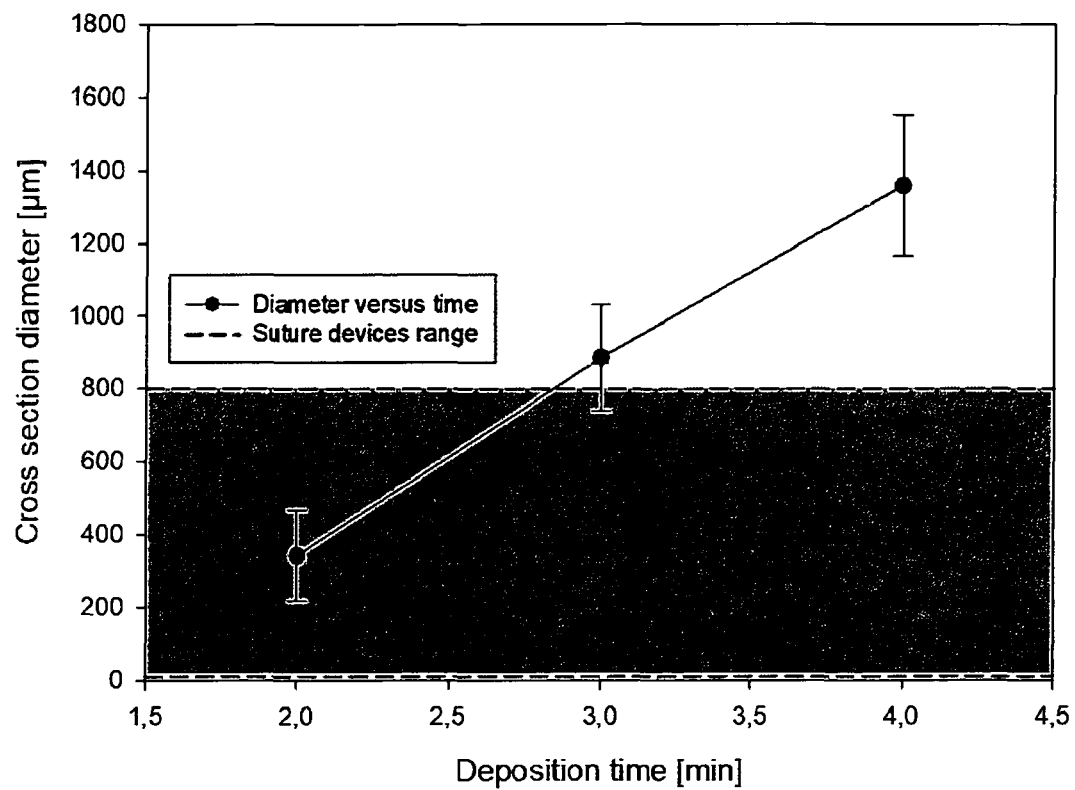
FIGS. 7A-7D: Diameter versus fibers deposition time characterization for optimized parameters set of FIG. 2 (FIG. 7A). Representative histological cross-section stained with Hematoxylin and Eosin for a sample in the 1200-1400 micrometer (μm) diameter range (FIG. 7B), 700-1100 μm diameter range (FIG. 7C), and 200-500 μm diameter range (FIG. 7D).

Diameter versus Fibers Deposition Time. The capacity of the presented method and apparatus can cover a range of interest for a surgical suture. Fiber diameter versus fiber deposition time was characterized for an optimized parameter set and apparatus according to FIG. 2. The cross section diameter (μm) as a function of deposition time was evaluated and showed that an increase in deposition time showed an increase in cross section diameter (FIG. 7A). A deposition time of 2 minutes and 3 minutes form ropes with a cross section diameter within the range of a surgical suture.

Figure 7B:
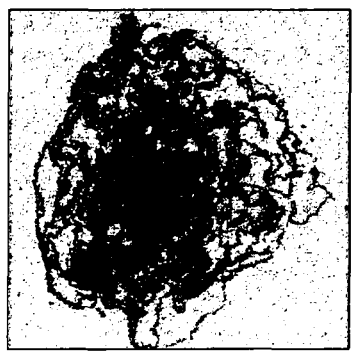
Figure 7C:
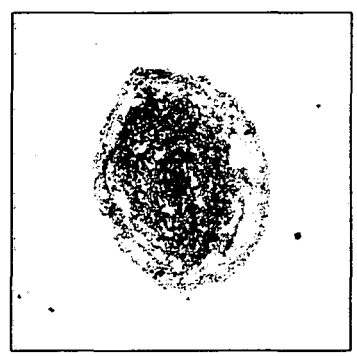
Figure 7D:
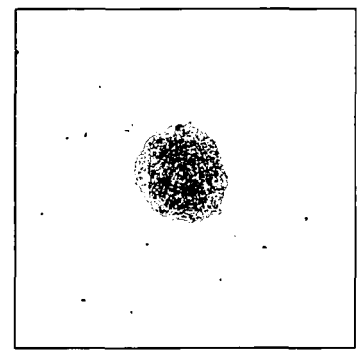

Histological cross-sections were obtained by staining with Hematoxylin and Eosin for ropes with a cross section diameter in the range of 1200 to 1400 μm (FIG. 7B), 700 to 1100 μm (FIG. 7C), and 200 to 500 μm (FIG. 7D). The circular cross-section of the histological images are dictated by the action of first motor and second motor, and the porous, fibrous nature of the processed rope.

Figure 8A:
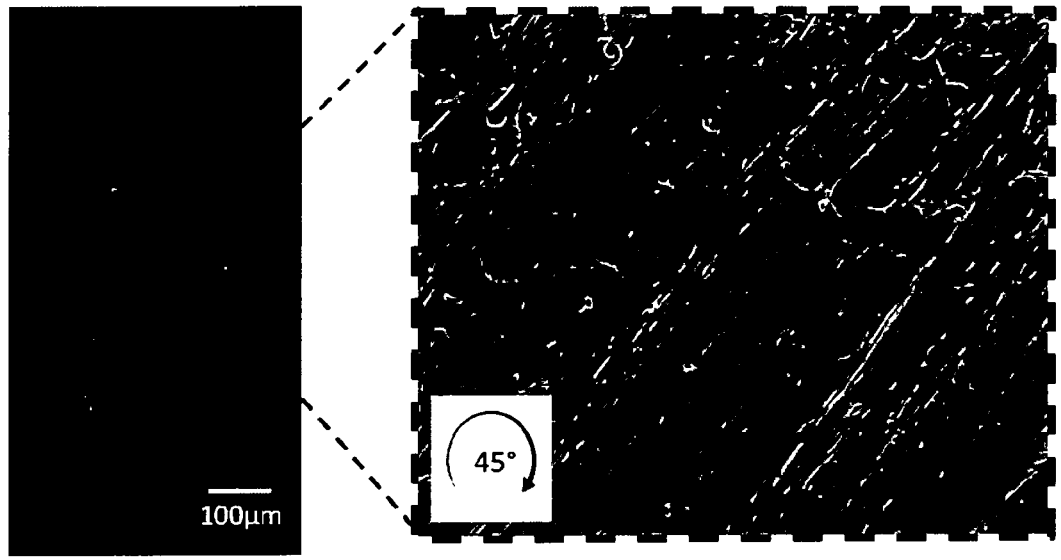
Figure 8B:
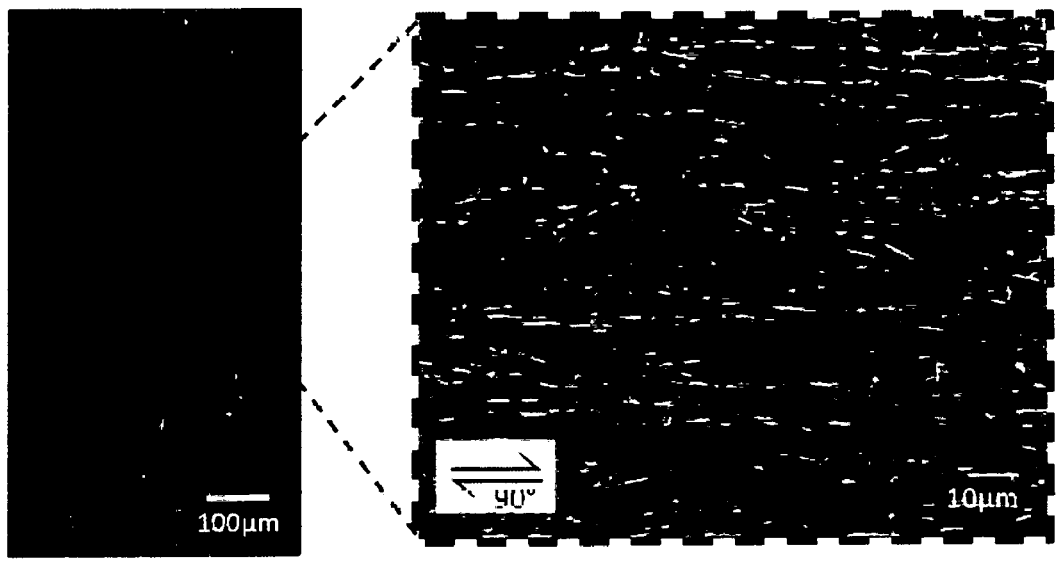
FIG. 8B is an SEM of a rope formed with the $\omega_1 = \omega_2$ configuration depicted in FIG. 5C.
Figure 8C:
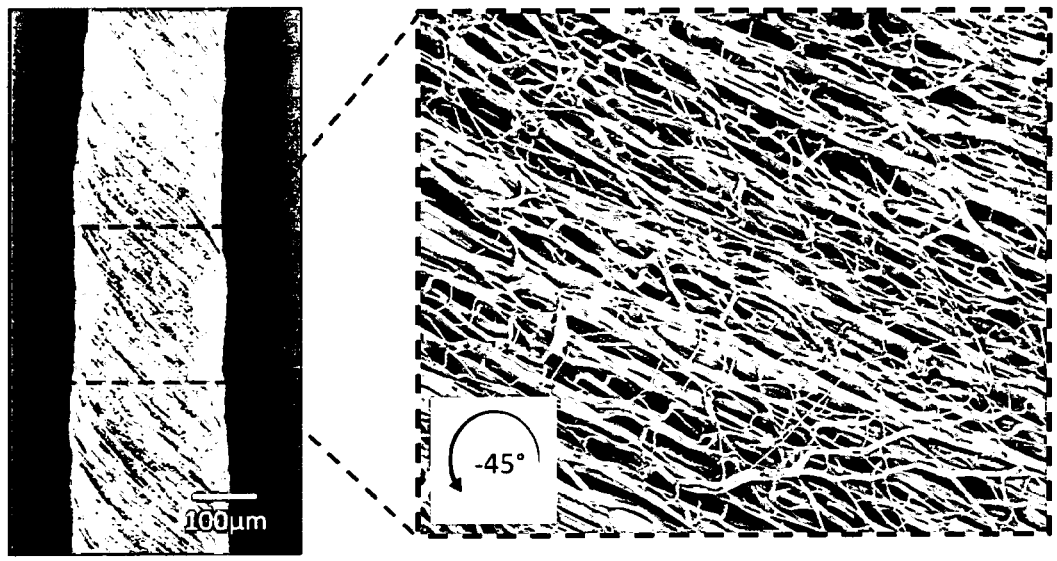
FIG. 8C is an SEM of a rope formed with the $\omega_1 < \omega_2$ configuration depicted in FIG. 5B.

Fiber Alignment. The alignment of fibers was evaluated with different motor velocities. As described in FIGS. 5A-5E, the ratio between the rotational speeds of the two electrodes dictates a different fiber arrangement. Representative SEM images were collected on ropes that were obtained using the three basic fabrication configurations. FIG. 8A depicts a rope obtained from a configuration of $\omega_1 > \omega_2$, where $\omega_1$ was 30 and $\omega_2$ was 0 rpm. The rope of FIG. 8B was obtained from a configuration of $\omega_1 = \omega_2$, where both w, and $\omega_2$ were 30 rpm. The rope of FIG. 8C had a configuration of $\omega_1 < \omega_2$, where $\omega_1$ was 0 rpm and $\omega_2$ was 30 rpm.

Figure 9A:
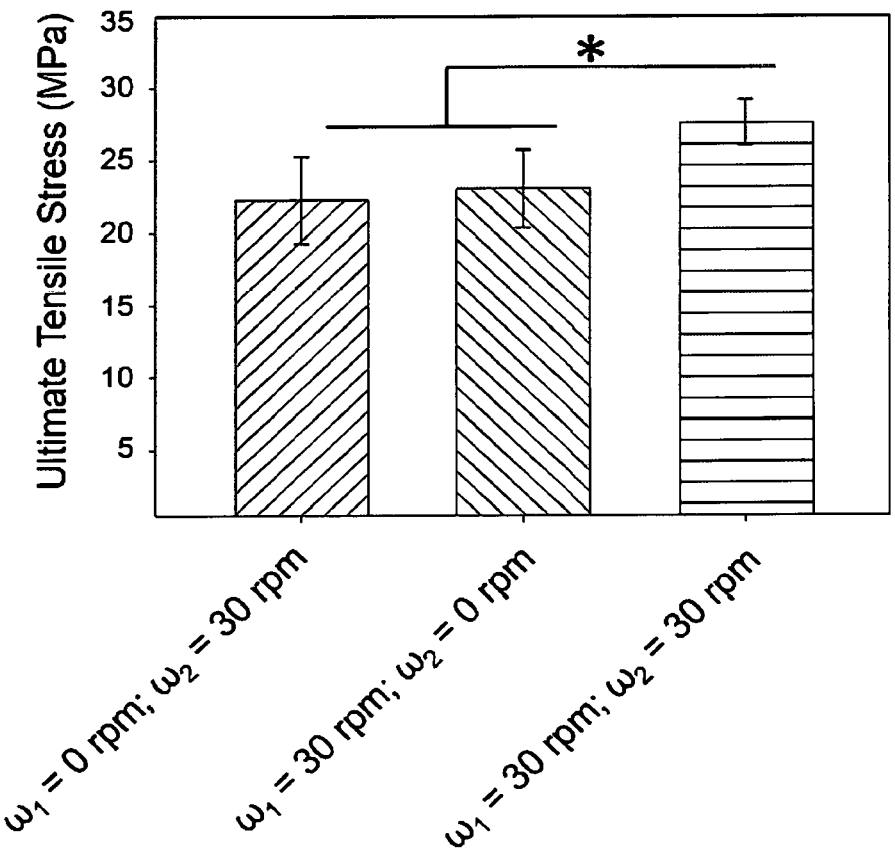
FIGS. 9A-9C are graphs depicting the uniaxial tensile mechanics of ropes obtained by processing at different motor velocities.
Figure 9B:
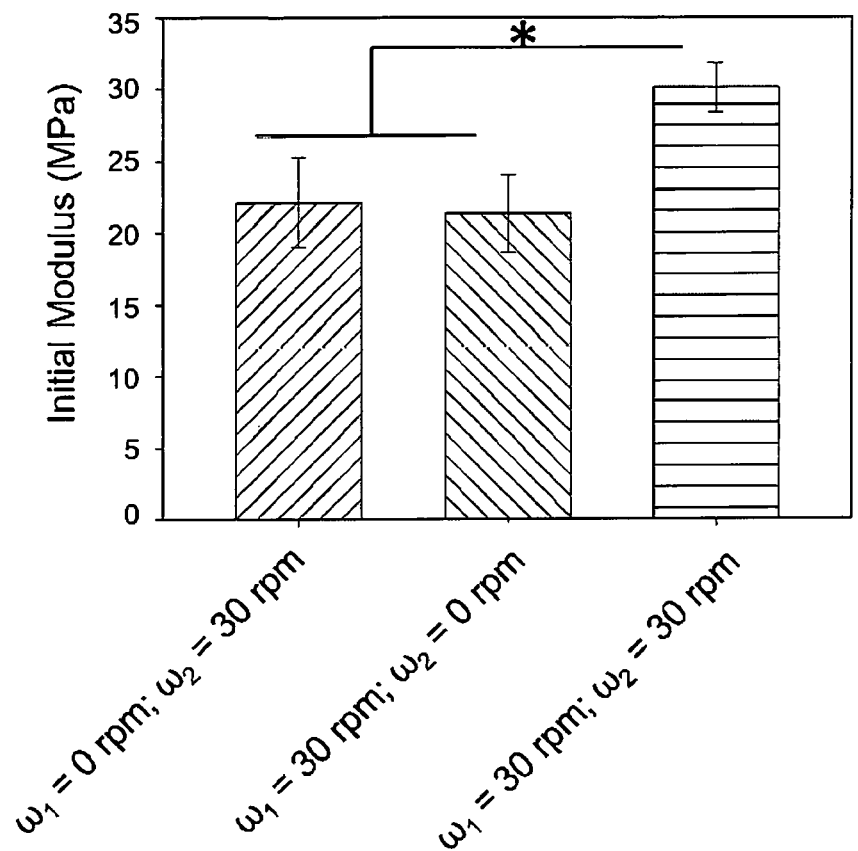
Figure 9C:
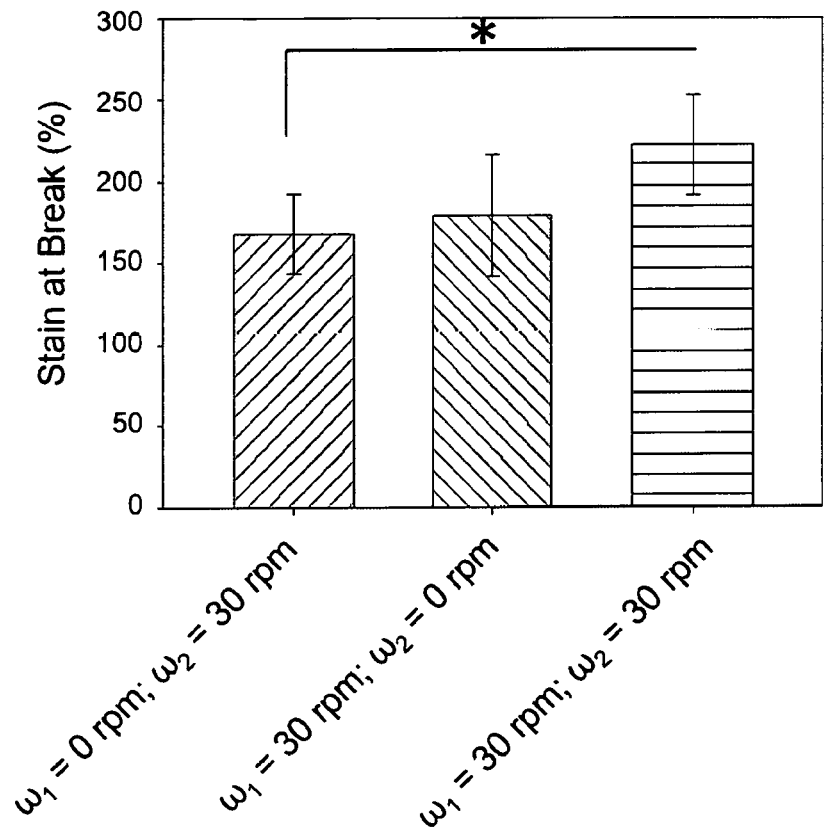

Uniaxial Tensile Mechanics. The ultimate tensile stress (FIG. 9A), initial modulus of elasticity (FIG. 9B), and strain at break (FIG. 9C) were obtained for the ropes of FIG. 8A, FIG. 8B, and FIG. 8C. The statistically significant differences (*) show the capacity to modify the rope uniaxial mechanics by changing the fiber arrangement while delivering the identical polymer mass during the deposition process.

EXAMPLE 3

Figure 10A:
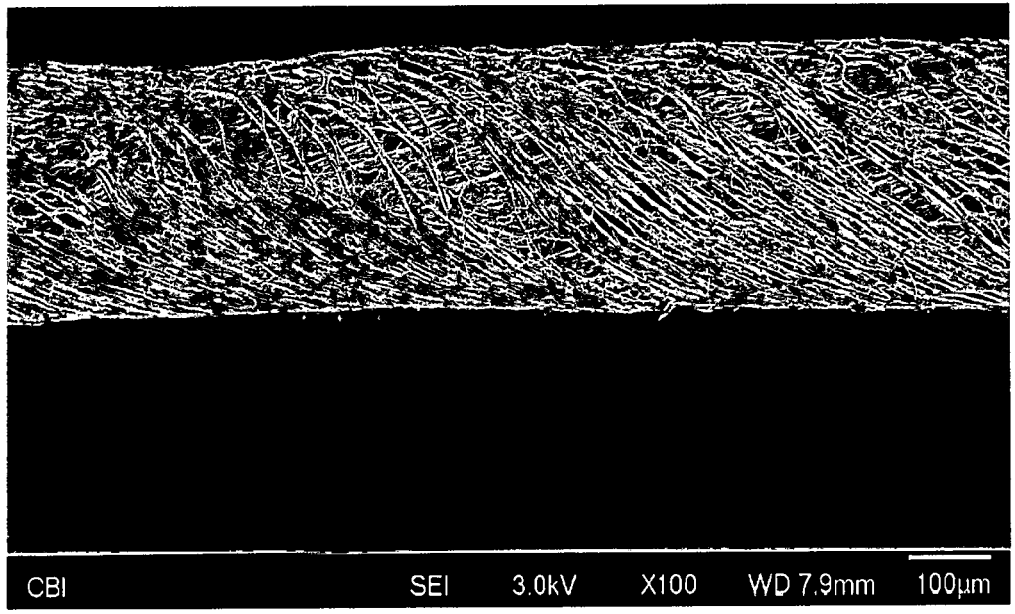
FIGS. 10A-10B are a representative SEM image (FIG. 10A) and schematic (FIG. 10B) of the rope obtained combining two or more fiber deposition configurations in sequence.
Figure 10B:
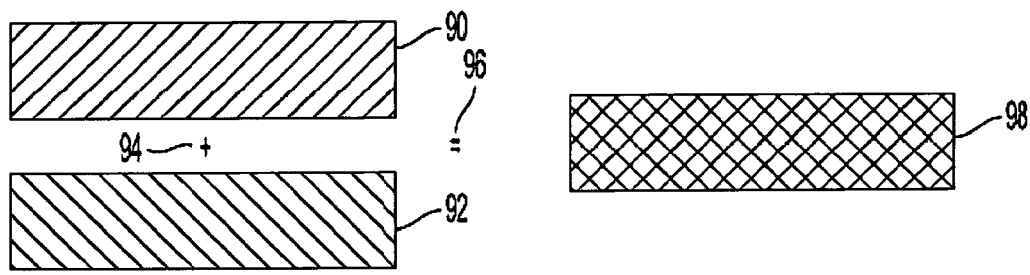

Multi-Layer Composite Rope. A multi-layer composite rope can be formed by combining two or more fiber deposition configurations in sequence. The SEM image depicted in FIG. 10A was formed from the combination of a $\omega_1 < \omega_2$ configuration and a $\omega_1 > \omega_2$ configuration (FIG. 10B). The core layer 90 of a polymer thread comprising aligned fibers has first a first twist angle and a first layer of a polymer 92 comprising aligned fibers having a second twist angle different from the first twist angle deposited over 94 at least a portion of the core layer 90, to form 96 a multi-layer composite rope 98.

EXAMPLE 4

Materials and Methods

Figure 11A:
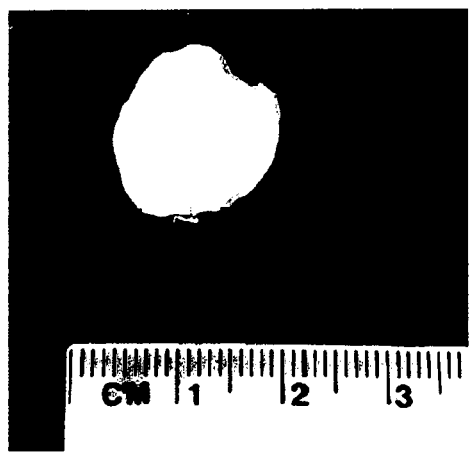
FIGS. 11A-11C are photographs of fabricated materials.

Electrospun Poly(ester urethane urea) Layer. A poly(ester urethane) urea (PEUU) layer (PEUU ES layer; FIG. 11A) was formed by electrospinning. The PEUU polymer was dissolved 12% weight by volume (w/v) in hexafluoroisopropanol (HFIP) the day before the layer fabrication. The PEUU ES layer was fabricated as previously described in D'Amore et al. (Bi-layered polyurethane—Extracellular matrix cardiac patch improves ischemic ventricular wall remodeling in a rat model. Biomaterials, 107:1-14 (2016)). Briefly, a steel 114 millimeter (mm) diameter cylinder with rotation speed of 750 rpm and rastering speed of 0.15 cm/min was used as a collecting target. The cylinder voltage was kept at −4 kV while rotating. The polymer solution flow rate was 20 ml/h, the needle was at 10 cm by the target and 13 kV charged. The PEUU ES layer was fabricated for 20 minutes and the PEUU ES layer dried under ambient condition in fume hood overnight.

Figure 11B:

Cast Poly(ester-urethane urea) disc. A cast PEUU disc (PEUU cast; FIG. 11B) was formed by depositing 4 milliliters (mL) of a 12% w/v PEUU solution (in HFIP) onto a clean Darlin round shaped container having a diameter of 13 centimeters (cm) and a flat surface. The PEUU was dried under a chemical fume hood overnight and removed from the container upon dryness. The discs used for the in vitro tests were obtained by cutting PEUU ES layer and PEUU cast with a 2 cm diameter punch. The discs were sterilized triple washed in ethanol 70% for 15 minutes each and triple washed in PBS for 15 minutes each, they were then exposed at UV light for 20 minutes.

Poly(ester-urethane)urea micro fiber-based suture wire fabrication. The processing method is based on the notion of mandrel-less deposition, previously introduced by the contributing author in International Patent Application Publication No. WO 2018/175234 A1 ("Mandrel-less Electrospinning Processing Method and System, and Uses Therefor"). In this study, moving electrodes and a rope coiling mechanism are introduced. Poly(ester-urethane)urea (PEUU) was synthesized as previously described (Guan, J. et al. Biodegradable poly (ether ester urethane) urea elastomers based on poly (ether ester) triblock copolymers and putrescine: synthesis, characterization and cytocompatibility, *Biomaterials* 25(1):85-96 (2004)) and the suture wires used in this study were fabricated with electrospinning using the developed apparatus described herein, such as the apparatus depicted in FIG. 2. The apparatus consists in two motors, one in the first head and one in the second head. Each motor controls the rotation of two mandrels ($\omega1$ and $\omega2$) around a common axis and allow start/stop and variable speed rotation. A direct current (DC) voltage is necessary for the electrospinning process. The mandrels are connected to an electrically conductive circuit, the voltage generated by the two facing electrodes will induce a deposition of microscopic polymer fibers. The polymer spinneret, connected to a voltage generator as well, is positioned between the two electrodes, polymer flow rate is controlled by a Harvard apparatus. The first head is also equipped with a third motor which is responsible for the motion of the spool present in the first head. The third motor in the first head and the spool are responsible for the micro fiber-based rope collection (take-up speed and direction can be controlled).

The PEUU polymer was dissolved 12% w/v in HFIP the day before the wire fabrication. The polymer voltage ($V_P$) was 10 kV and polymer flow rate set at 3 milliliters per hour (ml/h). The electrodes voltage ($V_G$) was 2 kiloVolts (kV), and the polymer needle-electrodes gap was 5 cm, with the same distance between the two electrodes.

Figure 11C:

Different microfiber depositions (90° ($\omega_1=\omega_2$), 45° ($\omega_1>\omega_2$), −45° ($\omega_1<\omega_2$), 90°/−45°/45°, −45°/45°/90°) were produced by changing the mandrel rotation. Herein described in detail the fabrication of the micro fiber-based rope used for the in vivo study. During the first step, the mandrels $\omega1$ and $\omega2$ ($\omega_1=\omega_2=30$ rpm) rotated with the DC voltage on and the spool mechanism was not in function, which allowed the first polymer deposition. After 3 minutes the polymer was macroscopically spanned from the two electrodes. The second step was the elongation in which the spool mechanism was functioning ($v_{spool}=2$ cm/min). The suture wires (FIG. 11C) were sterilized triple washed in ethanol 70% for 15 minutes each and triple washed in Phosphate-buffered saline (PBS) for 15 minutes each, they were then exposed at UV light for 20 minutes.

Cast Poly(ester-urethane)urea suture wire fabrication. The casted PEUU wire was obtained injected 12% w/v PEUU solution in a polytetrafluoroethylene (PTFE) 2.5 mm diameter tube and was allowed to dry under ambient condition in fume hood 48 hours.

Scanning Electron Microscopy: Surface characteristics of the PEUU ES suture wires were evaluated by scanning electron microscopy (SEM). The samples were sputter coated with 5 nm of gold-palladium and imaged using a JEM-6335F scanning electron microscope (Jeol, USA) at a working distance of 8 mm and magnifications of 100× and 1000×. The sample visual inspection was coupled with a complete fiber network topology quantitative analysis. Fiber diameter, orientation index and orientation angle were characterized with a custom-made algorithm developed with MATLAB (The Math-Works, Natick, MA) established by the contributing author of this work (D'Amore et al. "Characterization of the Complete Fiber Network Topology of Planar Fibrous Tissues and Scaffolds" *Biomaterials*, 31(2): 5345-5354 (2010)). SEM analysis was completed at 1000× magnification, with 21 images total and 7 per group were collected to characterize the PEUU ES wire ultrastructure.

Degradation of electrospun PEUU layer and PEUU cast. PEUU ES and PEEU cast layers were hydrolyzed using a modification of a previously established accelerated hydrolysis method (Molina, C. P. et al. Comparison of the host macrophage response to synthetic and biologic surgical meshes used for ventral hernia repair. *Journal of Immunology* 3:13-25 (2019)). PEUU ES and PEUU cast layers were cut in 1 centimeter (cm) by 1 cm pieces, weighed, and placed in a 50 ml conical tube. The discs were dissolved in 6.7% w/v 3 Molar (M) hydrochloric acid (HCl) at 37° C. and were shaken at 50 rpm for 30 days. Solubilized PEUU ES and PEUU cast released by the hydrolysis were neutralized to pH 7.0 with 10 M sodium hydroxide (NaOH). The resulting solutions were dialyzed for 24 hours with a 0.1-0.5 kiloDalton (kD) membrane (Float-A-Lyzer™ G2 Dialysis Device, Fisher Scientific Cat No. 08-607-016). The obtained PEUU degradation products were used to treat the bone marrow-derived macrophages, as described below.

Cell Culture and in vitro Analysis. Primary bone marrow macrophages were isolated from C57bl/6 mice as previously described (Englen, M. D. et al. Granulocyte/macrophage colony-stimulating factor is expressed and secreted in cultures of murine L929 cells. Journal of Immunological Methods, 184(2)281-3 (1995); Sicari, B. M. et al. The promotion of a constructive macrophage phenotype by solubilized extracellular matrix. *Biomaterials*, 35(30): 8605-8612, (2014)). All procedures were approved by and performed according to the guidelines of the Institutional Animal Care and Use Committee at the University of Pittsburgh. Briefly, female 6 to 8-week old C57bl/6 mice (Jackson Laboratories, Bar Harbor, ME) were euthanized via $CO_2$ inhalation and cervical dislocation in accordance with the guidelines of the American Veterinary Medical Association (AVMA) Panel of Euthanasia. Femurs, tibia, and fibula were harvested and washed three times in macrophage Complete Medium consisting of 10% FBS (Invitrogen, Carlsbad, CA), 10% L929 supernatant, 10 mM non-essential amino acids (Gibco, Grand Island, NY), 10 mM HEPES (Gibco), 2 mM L-glutamine (Gibco), 100 U/mL penicillin (Gibco), 100 mg/mL streptomycin (Gibco) and 0.1% β-mercaptoethanol in DMEM high glucose (Gibco). Complete medium was flushed through the medullary space of harvested bones and collected cells plated at $2 \times 10^6$ cells/mL into 12 and 6 well plates (Corning) for immunolabeling. PEUU ES sterile wires were seeded twice, each with 20 microliters (μl), at $10 \times 10^6$ cells/mL per scaffold. For immunoblotting studies, $5 \times 10^6$ cells were seeded onto the surface of 2 cm diameter sterile discs of either PEUU cast and PEUU ES layers. Medium was supplemented 24 h after plating, cells were differentiated into macrophages for 7 days at 37° C. and 5% $CO_2$ with media changes every 48 hours.

In vitro macrophage activation with degraded PEUU ES layer or PEUU cast. Bone marrow macrophages were isolated and cultured as described above. After 7 days, naïve macrophages were stimulated with 1:10 or 1:50 dilution of PEUU cast degradation products, or 1:10 or 1:50 dilution of PEUU ES layer degradation products for immunolabeling studies or 1 ml of the following macrophages activation controls: complete media (M0), 20 ng/ml IFN-γ+100 ng/ml LPS (M1), 20 ng/ml IL-4 (M2). Treated macrophages were incubated for 16 hours at 37° C. and 5% $CO_2$.

Immunolabeling of in vitro treated macrophages. After 16 hours of incubation, stimulated macrophages were washed with PBS and fixed for 20 minutes at room temperature with 4% paraformaldehyde (PFA). PEUU ES seeded wires were collected and fixed in 10% neutral-buffered formalin and embedded in paraffin. Sections of 5 μm were cut and mounted onto glass slides. To prevent non-specific binding, fixed cells and wire sections were incubated in a blocking solution composed of PBS, 0.1% Triton-X, 0.1% Tween-20, 4% goat serum and 2% bovine serum albumin (BSA) for 1 h at room temperature. Blocking buffer was then removed, stimulated macrophages and sections were incubated at 4° C. for 16 hour in a solution of one of the following primary antibodies: 1) monoclonal anti-F4/80 (Novus) at 1:200 dilution as a pan-macrophage marker; 2) polyclonal anti-inducible nitric oxide synthase (iNOS) (Abcam, Cambridge, MA) at 1:100 dilution as an M1-like marker, and 3) anti-Arginase1 (Abcam, Cambridge, MA) at 1:200 dilution, as an M2-like marker. Primary antibodies were removed and after PBS washing a solution of fluorophore-conjugated secondary antibodies (Alexa donkey anti-rabbit 488 or donkey anti-rat 488; Invitrogen, Carlsbad, CA) were added to the appropriate well/section for 1 h at room temperature. The antibodies were then removed, the cells washed with PBS, and the nuclei were counterstained using 4',6-diamidino-2-phenylindole (DAPI). Cytokine-activated macrophages were used to establish standardized exposure times (positive control), which were held constant throughout groups thereafter. Images of three 20× fields were taken for each well using a Zeus live-cell microscope. CellProfiler (Broad Institute, Cambridge, MA) was used to quantify images. Data were analyzed for statistical significance using a one-way analysis of variance with Tukey's post-hoc test for multiple comparisons.

Immunoblotting. After 7 days of differentiation, the expression of macrophage activation markers was evaluated on macrophages seeded on discs of either PEUU cast or PEUU ES layers and macrophages on tissue culture plastic controls. As controls of macrophages activation, cells were treated as follows: 100 nanograms per milliliter (ng/mL) LPS (Sigma Aldrich, USA) and 20 ng/mL IFN-γ (Peprotech, USA) to induce M1 macrophage activation, 20 ng/mL IL-4 to induce M2 macrophage activation. After 16 hours of induced activation, the treatments were removed and the stimulated macrophages and seeded PEUU discs were washed with PBS. Cells seeded in the tissue culture plastic were scraped, collected, and centrifuged. PEUU ES layer and cast discs were collected in a 1 ml Eppendorf tube. Samples were subsequently lysed in RIPA buffer supplemented with protease inhibitor cocktail. Lysates were then quantified using BCA (Bio-Rad). 10 mg total protein in Laemmli buffer containing 5% β-mercaptoethanol were loaded to 4-20% polyacrylamide MiniPROTEAN TGX precast gels (Bio-Rad) and run at 150 V for ~45 minutes in Tris-Glycine running buffer. Upon completion, wet transfer was performed using polyvinylidene difluoride membranes in Tris-Glycine transfer buffer with 20% methanol at 350 mAmp on ice. After 45 minutes, membranes were removed from the transfer chamber, washed for 10 minutes in Tris-buffered saline, 0.1% Tween 20 (TBST) and blocked for 1 h in TBST with 5% bovine serum albumin (Sigma). After blocking, membranes were incubated overnight at 4° C. with: 0.1 mg/ml mouse-anti-β-actin (sc-47778, Santa Cruz Biotechnologies, Dallas. TX), 0.1 mg/ml rabbit-anti-arginase 1 (ab91279, Abcam), or 0.1 mg/ml rabbit-anti-iNOS (inducible nitric oxide synthase) (PA3-030A, Thermo Fisher). Following primary antibody incubation, membranes were washed 3× in TBST and subsequently incubated for 1 h at room temperature with goat-anti-rabbit HRP-conjugated antibodies (Dako Affinity Purified; Agilent, Santa Clara, CA) diluted 1:1000 in TBST with 5% BSA. Membranes were then washed 3× with TBST and incubated in chemiluminescent substrate (Clarity ECL Substrate; Bio-Rad) for 5 minutes and subsequently imaged (ChemiDoc Touch; Bio-Rad). Acquired images were analyzed using ImageJ and all groups were normalized to the appropriate loading control. N=3 biological replicates, densitometry results were averaged across replicates and means were compared.

Surgical procedures and In vivo studies of the electrospun PEUU suture wire. All procedures were approved by and performed according to the guidelines of the Institutional Animal Care and Use Committee at the University of Pittsburgh. A number of 20 female Sprague Dawley rats >2 months of age were used for evaluation of host response to suture materials testing, with 4 animals used per each test material. Briefly, the rats were anesthetized using 1-3% inhaled isoflurane until signs of consciousness could not be elicited. The hair overlying the dorsum of the animals was removed, and the animals were placed prone on a warming pad while receiving inhaled isoflurane. The skin was cleansed using betadine and ethanol, allowed to dry, and a 2 cm incision was made between the scapulae. The skin was subsequently closed using two interrupted sutures composed of one of the following materials: Polyglycolic Acid (PGA), Polydioxanone (PDS), Polypropylene (PPL), PEUU cast wire, or PEUU ES wire. Animals were survived for either 14- or 30-days post-surgery and subsequently sacrificed in accordance with the guidelines of the American Veterinary Medical Association (AVMA) Panel of Euthanasia.

At 14 and 30 days, the hair from the dorsal skin. Next, an area of 5 cm by 5 cm section around the treated skin and underlying connective tissue was harvested. At 14 days, the scar area was harvested, fixed in 10% formalin, and paraffin embedded for histological evaluation. At 30 days, the incision was divided in two parts, upper side was used for the histological evaluation and the bottom side for the biaxial mechanical evaluation. The suture materials, where present, were collected and analyzed by uniaxial mechanical testing. The samples for the mechanical evaluation, either uniaxial and biaxial tests, were flash frozen in isopentane cooled in dry ice for 1 minute. Frozen samples were stored at −80° C. for 1 week, thawed at 4° C. overnight, and raised in PBS for 1 hour before testing (Chen, S. et al. A microstructurally inspired constitutive model for skin mechanics. *Biomechanics and Modeling in Mechanobiology*, 19(1):275-289 (2020)).

Uniaxial Mechanical testing of suture materials pre- and post-implantation. The suture materials, where present, were subjected to uniaxial stress pre- and post-implantation, as compared to the rat skin mechanical properties. All the uniaxial tensile tests were performed on a horizontal MTS Tytron™ 250 machine. Samples were subjected to 0.75 N preload and strained at a speed of 25 mm/min until failure to determine the complete stress/strain curve. Samples were tested following the D2256/D2256M Standard Test Method for Tensile Properties of Yarns by the Single-Strand Method. Before the uniaxial tests, the sample diameters were measured using a Zeus live-cell microscope. The PEUU ES wires with different fiber arrangement were tested 24 hours after the fabrication. The suture wires collected after the in vivo study were tested immediately after harvesting. Rat dorsal skin between the scapulae was collected from 2 animals as a control. The skin was cut with a dog bone-shaped punch with 2 samples collected from each animal. Samples were cut in the longitudinal direction (i.e. direction parallel to the spine).

Biaxial Mechanical testing of rat skin. A custom-built planar biaxial stretching system was used to determine mechanical properties of rat skin. Samples were cut in square shape, 10 mm by 10 mm which contained the sutured area. Prior to mounting, the subcutaneous layer and any remaining panniculus carnosus was carefully removed from the samples for biaxial testing. Markers were placed on the corners of a squared area at the center of the sample and used to measure the deformation gradient tensor. Tests were performed using a Lagrangian equi-stress control protocol and a maximum load of 250 kilopascal (kPa) (Shang, X. et al. Studies of biaxial mechanical properties and nonlinear finite element modeling of skin. *Molecular and Cellular Biomechanics* 7(2):93 (2010)) was adopted to induce physiologically relevant strain levels. Samples were preconditioned and then tested for 10 cycles of 15 seconds in PBS at room temperature. Data processing was performed with a custom-made software developed in Matlab using the free float position of the markers following preconditioning as a reference as previously described in D'Amore et al. 2016.

Histology: Masson's Trichrome staining and collagen quantification. Embedded samples and healthy rat skin controls were transversely sectioned to a thickness of 5 μm and stained with Masson's Trichrome in order to evaluate newly formed tissue, cellular infiltration, and scar area. Images of each sample 5× magnification were collected using a Zeus live-cell microscope. The explant visual inspection was coupled with quantitative measurements. NIH Image J (NIH, Bethesda, MD; https-/imagej.nih.gov/ij) software for image analysis was utilized to cut the area among the region of interest identifying the sutured area in the sample images. To assess the foreign body response, a custom-made algorithm, developed in MatLab (Math-Work, Natick, MA), was utilized as previously described (D'Amore et al. Nitro-Oleic Acid (NO2-OA) Release Enhances Regional Angiogenesis in a Rat Abdominal Wall Defect Model. *Tissue Engineering Part A*, 24(11-12) (2018)) to segment and quantify collagen rich areas.

Immunolabeling of rat skin sections. Embedded samples and healthy rat skin controls were transversely sectioned to a thickness of 5 μm and mounted onto glass slides. Slides were deparaffinized using xylene and ethanol gradients (100-70% EtOH). Immunofluorescence was performed on serial sections for each subject and timepoint to assess the phenotypes of immune and satellite cell populations. After deparaffinization, the slides were placed in citrate antigen retrieval buffer (10 mM citric acid monohydrate, pH 6.0), microwaved at 100% power for 45 seconds, followed by 15 minutes at 20% power. The slides were then cooled in copper sulfate solution (10 milliMolar (mM) $CuSO_4$, 50 mM ammonium acetate, pH 5.0) for 20 minutes. Sections were then rinsed three times in Tris buffered saline/Tween 20 solution (TBST) and then incubated for 1 hour at room temperature in blocking buffer containing 0.1% Triton-X 100, 0.1% Tween, 2% goat serum, and 1% bovine serum albumin. The blocking buffer was then removed and the sections were incubated overnight at 4 degrees Celsius (° C.) in a humidified chamber with 1:200 rabbit-anti-CD11b (Abcam), a pan-macrophage marker. Following overnight incubation, each slide was washed in TBST for 3×2 minutes. A 1:200 solution of goat-anti-rabbit horseradish peroxidase conjugated secondary antibody (DAKO) in blocking buffer was subsequently applied and microwaved at 40% power for 3 minutes in a humidified chamber and allowed to cool for 2 minutes before washing in TBST. After washing, sections were incubated with a 1:200 solution of red fluorescent HRP substrate (OPAL 570, Perkin Elmer) in 1× Amplification Diluent (Perkin Elmer) for 10 minutes and then washed in TBST. To remove anti-CD11b and anti-rabbit antibodies, sections were subjected to a second round of antigen retrieval in citrate antigen retrieval buffer, followed by cooling copper sulfate solution, and blocked as described above. For each slide, one section was incubated with a 1:200 solution of rabbit-anti-iNOS antibody (Invitrogen) in blocking buffer, and one section was incubated with a 1:200 solution of rabbit-anti-RELMa (PeproTech). Slides with the primary antibodies were then placed on a raised waterbath and microwaved at 40% power for 3 minutes, followed by 2 minutes of cooling. Slides were then washed in TBST solution and a 1:200 solution of goat-anti-rabbit HRP-conjugated secondary antibody was placed on the sections. Slides with secondary antibody solutions were then placed in the waterbath and microwaved at 40% power for 3 minutes, followed by 2 minutes of cooling. After cooling, slides were washed in TBST and a 1:200 solution of green fluorescent HRP substrate in 1× Amplification Diluent (520 Opal, Perkin Elmer) was placed over each section and incubated in a dark humidified chamber for 10 minutes at room temperature. The sections were then washed in TBST, incubated with 4',6-diamidino-2-phenylindole (DAPI) nuclear counterstain for 5 minutes. The sections were washed with TBST and subsequently mounted for imaging by fluorescence microscopy.

Statistical Analysis. Statistical analyses were performed using SigmaPlot version 14.0 (Systat Software Inc., Chicago, IL, USA) and GraphPad Prism version 8 (GraphPad Software, La Jolla CA, USA). The mean value differences between groups, and whether the differences were significant, were determined by either a one-way Analysis of Variance (ANOVA) with a post-hoc Tukey HSD (honestly significant difference) test, for data with normal distribution, or a Welch ANOVA and Brown-Forsythe test with Dunnett T3 post hoc test, for data with not normal distribution. All data are presented as mean±standard error of mean (SEM). Significance level was set at $p<0.05$.

Results and Discussion

Figure 12A:
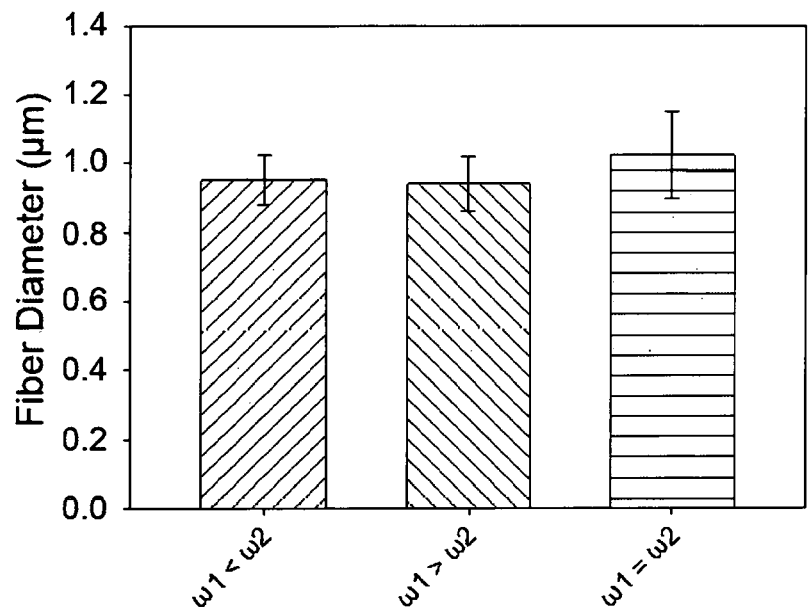
FIGS. 12A-12D are graphs depicting the fiber diameter (FIG. 12A), the orientation index (FIG. 12B), the orientation angle (FIG. 12C), and the initial modulus of elasticity in MPa (FIG. 12D) of PEUU ES wires deposited at different deposition angles (based on the fiber collection spool rotation). The control in FIG. 12D is PEUU cast wire. One Way ANOVA shows statistically significant differences among the groups, *=$p<0.05$
Figure 12B:
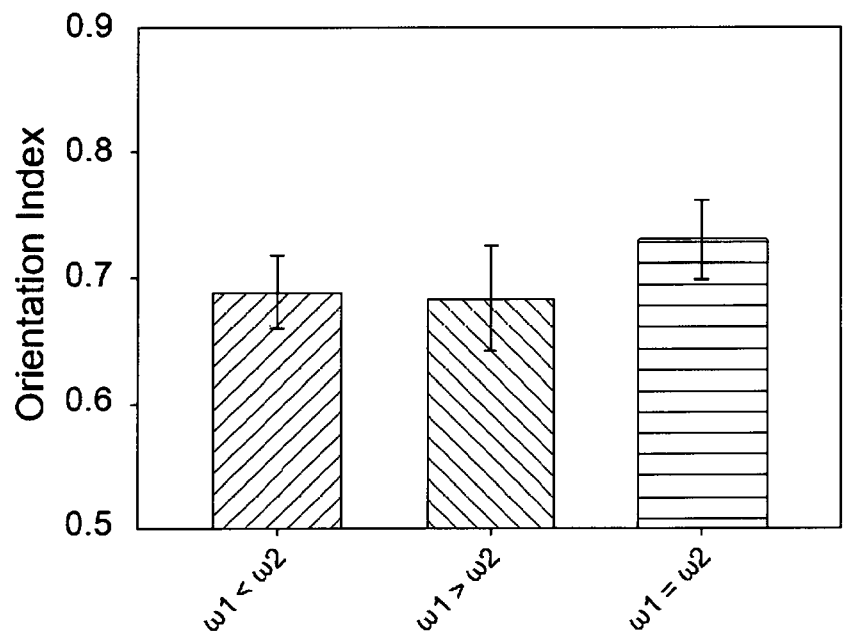
Figure 12C:
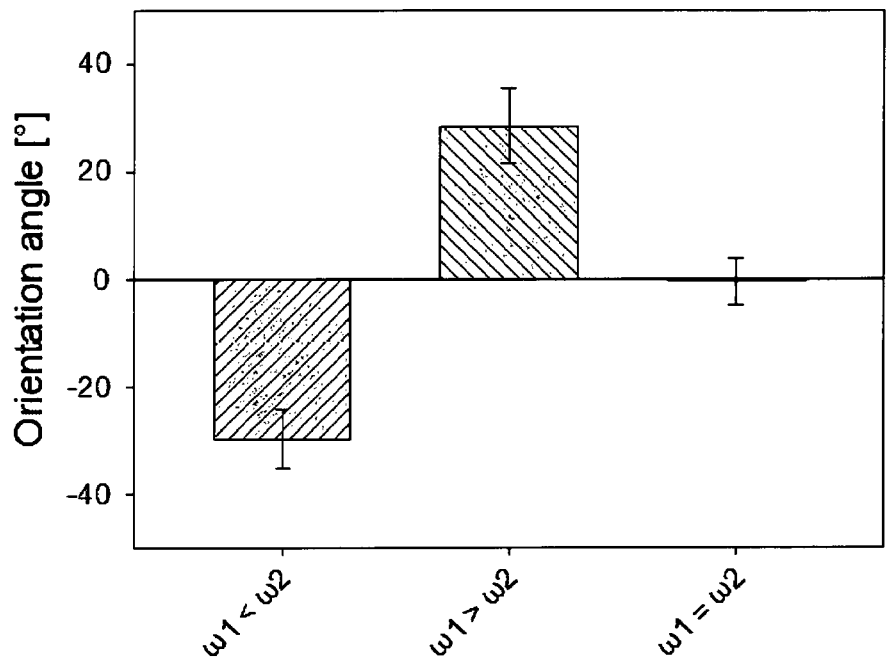

Electrospun PEUU Layer, PEUU cast, and PEUU ES suture wire materials characterization. The resulting PEUU ES layer had an average thickness of 0.04±0.02 mm. The resulting PEUU cast had an average thickness of 0.029±0.007 mm. A fabrication time of 20 minutes produced a round cross sectioned PEUU ES suture wire 32 cm in length with a diameter of 0.834±0.248 mm. Representative SEM images for the 45° ($\omega_1 > \omega_2$), 90° ($\omega_1 = \omega_2$), and −45° ($\omega_1 < \omega_2$) suture wire orientations can be found in FIGS. 8A-8B. The fiber diameter, orientation index, and orientation angle of PEUU ES wires are graphically represented in FIGS. 12A-12C, respectively. One-way ANOVA statistical testing determined that there is no significant difference between the resulting fiber diameters for the 45° ($\omega_1 > \omega_2$), 90° ($\omega_1 = \omega_2$), and −45° ($\omega_1 < \omega_2$) suture wire orientations (FIG. 12A). The orientation index shows the influence of the specific manufacturing parameters (FIG. 12B). The orientation angle (FIG. 12C) was determined by $\cos^2$(orientation index) and provides further evidence for the differences that can be achieved by the different manufacturing characteristics.

Figure 12D:
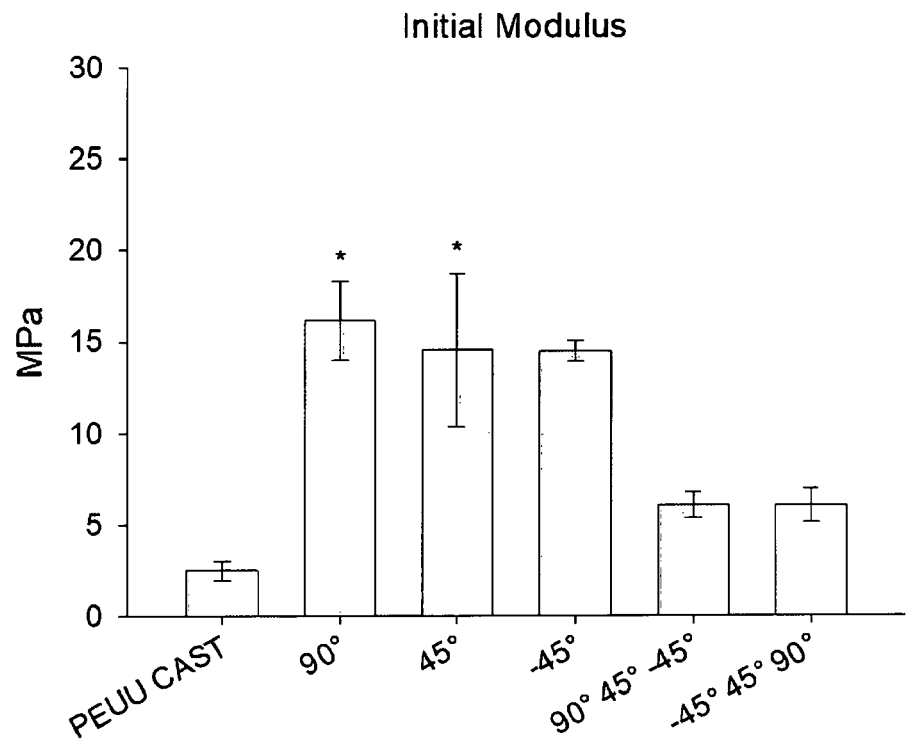

Mechanical Testing of PEUU-ES wires. The initial modulus of elasticity for PEUU-ES wires at different depositions, as compared to the PEUU cast wire material, is graphically represented in FIG. 12D. Uniaxial tensile test results show the capacity to modify the wire mechanical properties by changing the fiber arrangement while delivering the identical polymer mass during the deposition process. One Way ANOVA shows statistically significant differences among the groups, *=p<0.05.

Figure 13A:
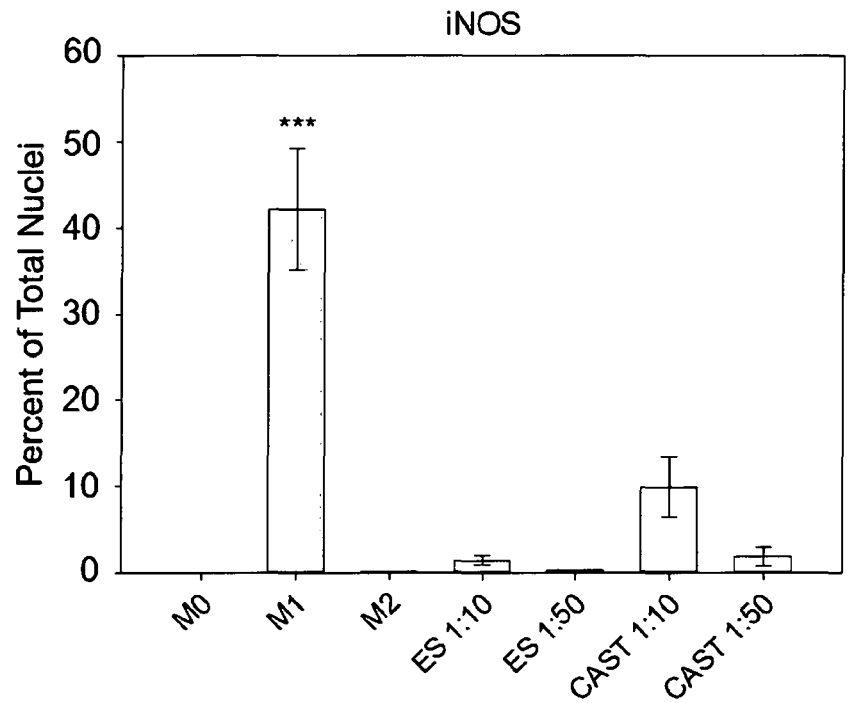
FIGS. 13A-13O depict the quantitative results of activated macrophages phenotype evaluated by immunolabeling. Activation of markers associated with pro-inflammatory (iNOS, FIG. 13A) and anti-inflammatory Fizz1 (FIG. 13B) and Arginase1 (FIG. 13C) phenotypes was evaluated by immunolabeling. A general marker of macrophages (F4/80), was used. Known factors that are promoters of pro-inflammatory (100 ng/ml LPS and 20 ng/ml IFN-γ) or anti-inflammatory (20 ng/ml IL-4) phenotypes were included as controls. Quantification of the response of treated macrophages. Images were quantified using Cell Profiler image analysis software. Differences between stimuli for each marker were evaluated using non-parametric ANOVA test. One Way ANOVA shows statistically significant differences among the groups, ***=p<0.001.
Figure 13B:
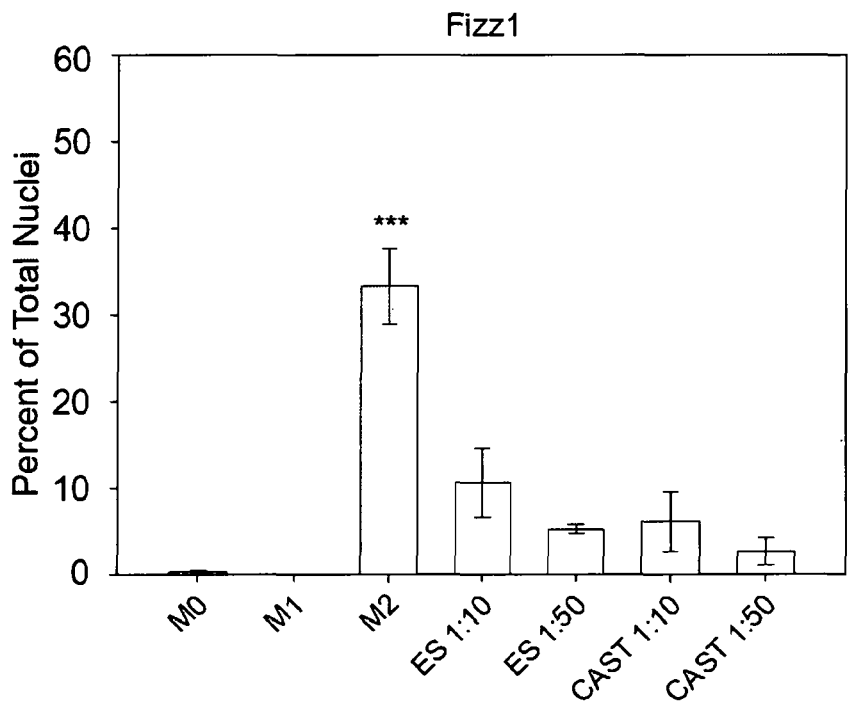
Figure 13C:
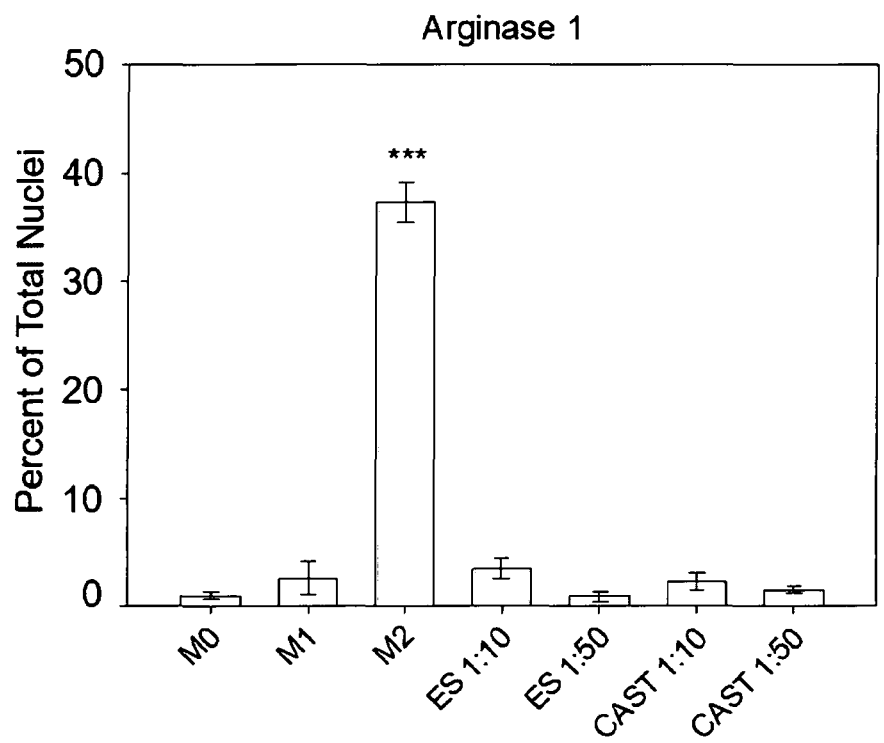

In vitro macrophage differentiation with degraded PEUU products. Activated macrophages phenotype were evaluated by immunolabeling (results not shown). Activation of markers associated with pro-inflammatory (iNOS, FIG. 13A) and anti-inflammatory (Fizz1 (FIG. 13B) and Arginase1 (FIG. 13C)) phenotypes was evaluated by immunolabeling. A general marker of macrophages (F4/80), was used. Known factors that are promoters of pro-inflammatory (100 ng/ml LPS and 20 ng/ml IFN-γ) or anti-inflammatory (20 ng/ml IL-4) phenotypes were included as controls. The quantification, using Cell Profiler image analysis software, of the response of treated macrophages can be found in FIGS. 13A-13C. Differences between stimuli for each marker were evaluated using a non-parametric ANOVA test, which shows statistically significant differences among the groups.

Figure 14A:
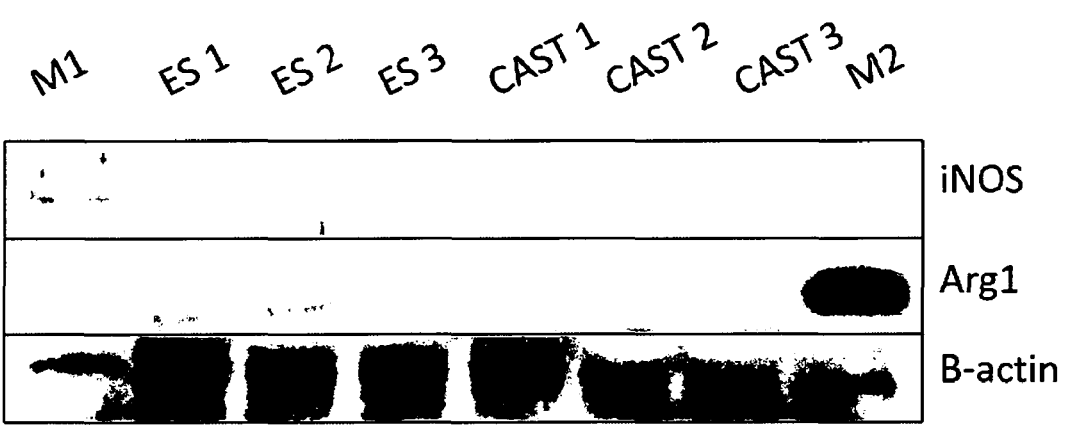
Figure 14B:
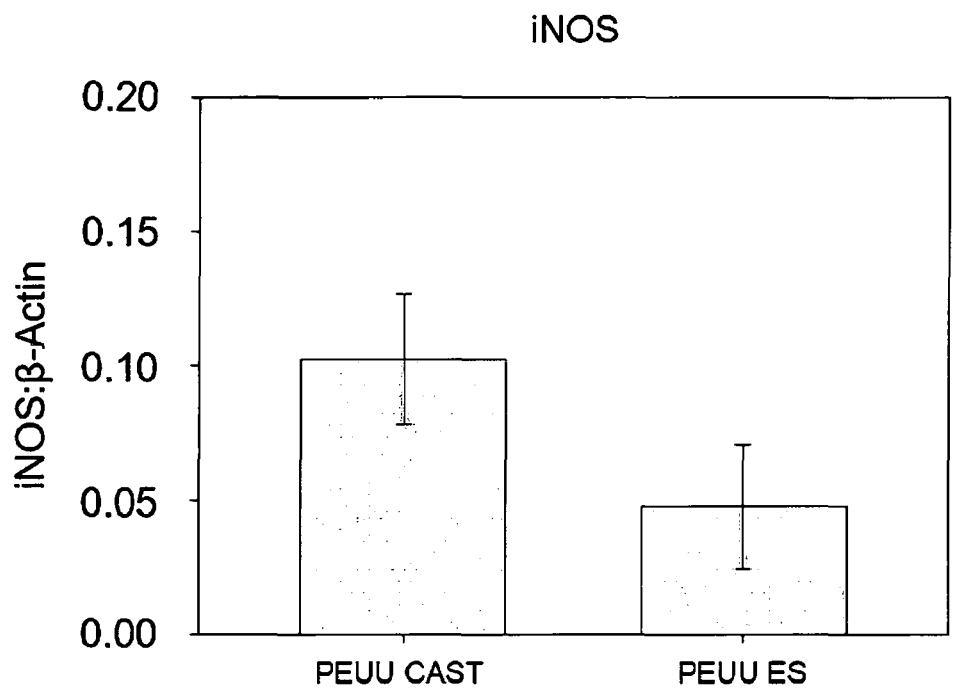
FIGS. 14B and 14C show the densitometry quantification of pro- and anti-inflammatory protein expression iNOS (FIG. 14B) and Arginase1 (FIG. 14C) normalized to the β-actin. One Way ANOVA statistical test shows statistically significant differences between means, *=p<0.05.
Figure 14C:
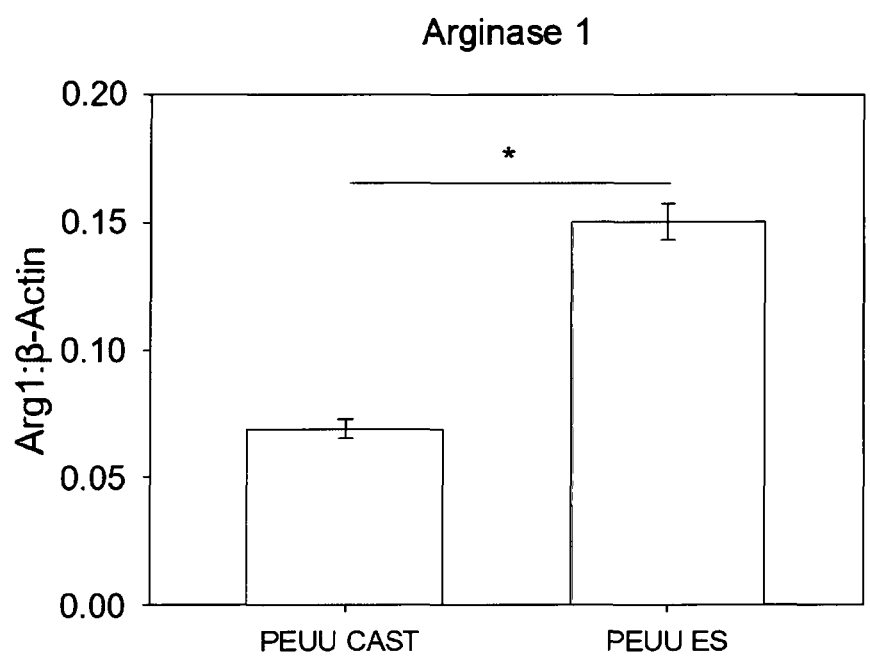
Figure 14D:
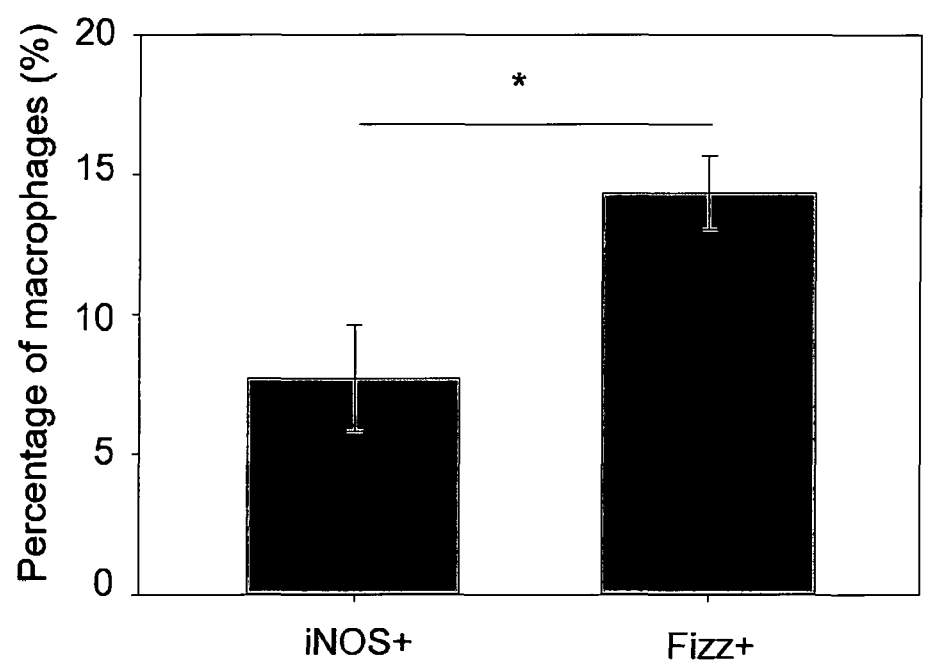
FIG. 14D shows PEUU ES wire immunolabeling quantitative analysis.

In vitro macrophage differentiation with PEUU ES or PEUU cast layers. The macrophage protein expression for PEUU ES and PEUU cast layers can be found in FIGS. 14A, 14B, 14C, and 14D. The resulting Western-Blot of iNOS and Arginase expression can be found in FIG. 14A. FIGS. 14B and 14C show the densitometry quantification of pro-and anti-inflammatory protein expression iNOS (FIG. 14B) and Arginase1 (FIG. 14C) normalized to the ß-actin, where one Way ANOVA statistical test shows statistically significant differences between means. FIG. 14D indicates that macrophages grown on the PEUU ES showed a higher expression of arginase 1, or the M2 associated marker, where the one Way ANOVA statistical test shows statistically significant differences between means.

Figure 15A:
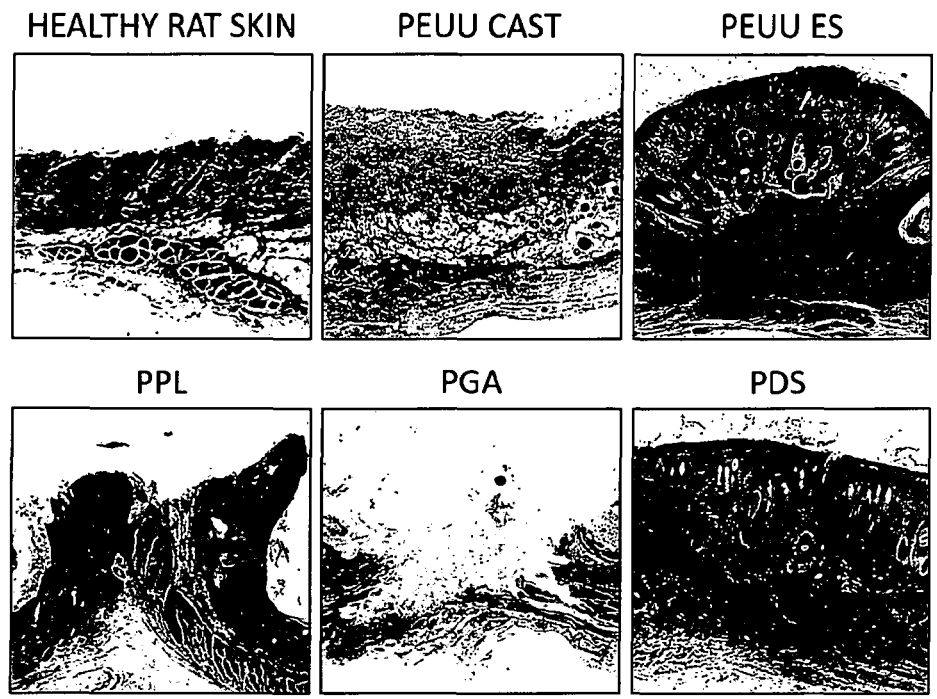
FIGS. 15A-15B depict a qualitative histological evaluation. Masson's Trichrome staining was used to evaluate the ex novo tissue, cellular infiltration and scar formation of 30-days explants compared to healthy rat tissue (FIG. 15A). The Masson's Trichrome staining was originally collected in color.
Figure 15B:
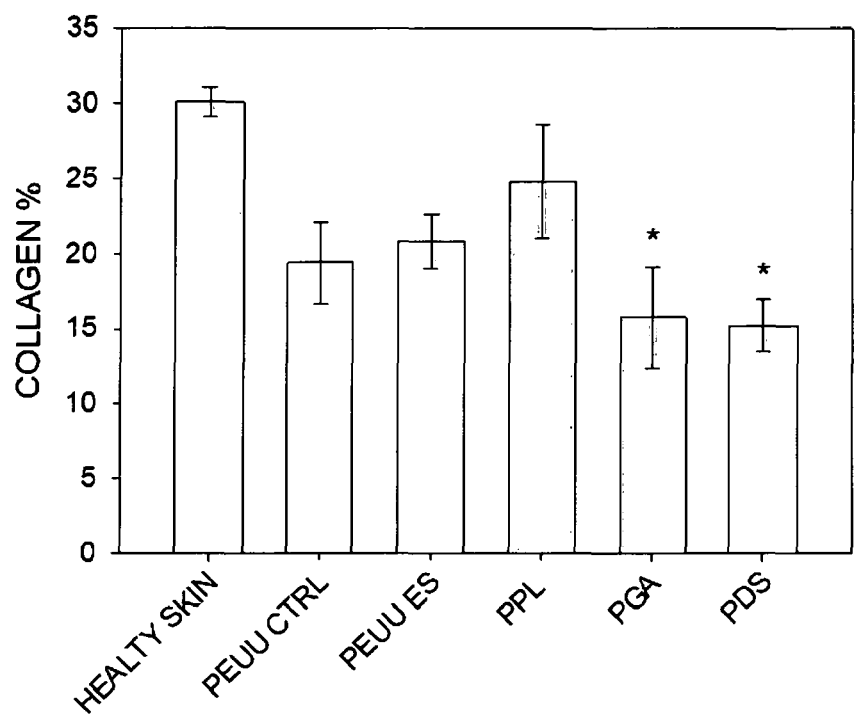

Collagen remodeling. Masson's Trichrome staining (FIG. 15A) was used to evaluate the ex novo tissue, cellular infiltration, and scar formation of 30-days explants compared to healthy rat tissue. The average collagen percentage under the 30-days sutured area was compared to normal skin collagen percentage and one Way ANOVA analysis showed statistically significant differences among the groups (*=p<0.05) (FIG. 15B).

Figure 16A:
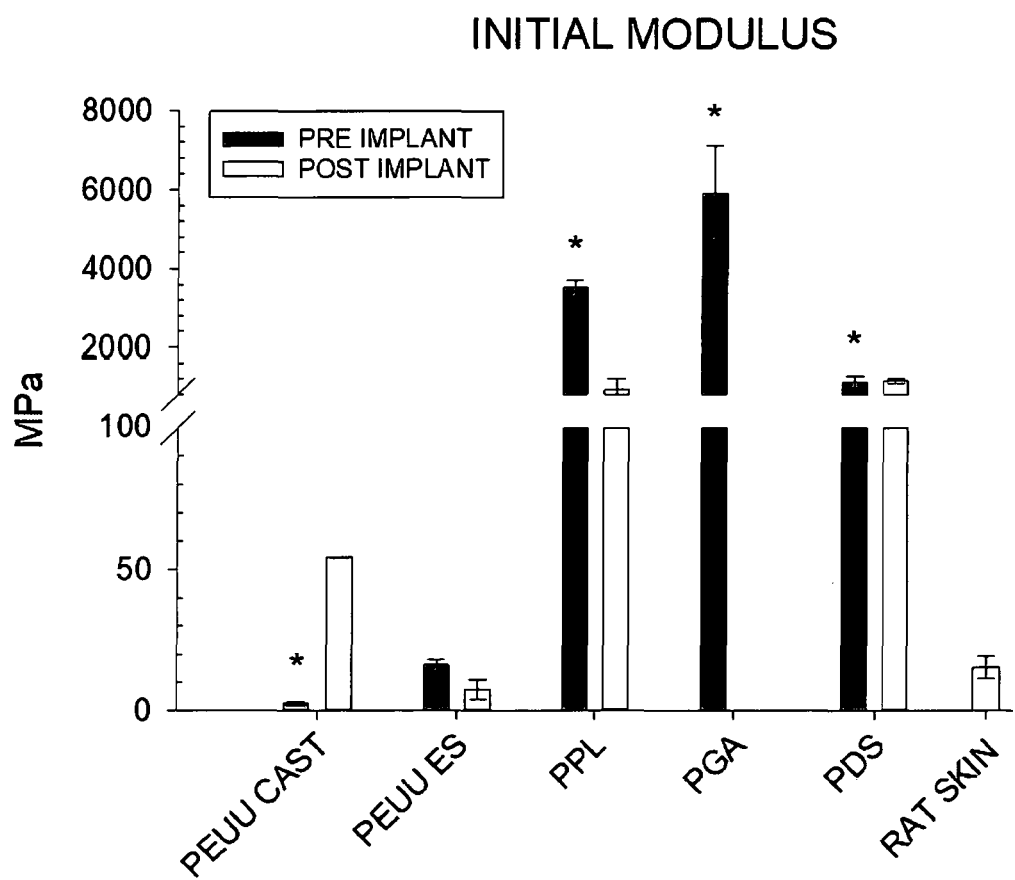
FIGS. 16A-16C are graphs depicting the uniaxial tensile mechanics of PEUU cast wire, PEUU ES wire, PPL, PGA, and PDS sutures pre- and post-implantation.

Mechanical testing of pre- and post-implant suture materials. The results for the initial modulus of the PEUU cast wire, PEUU ES wire, PPL, PGA, and PDS suture wires pre- and post-implantation can be found in FIG. 16A. The pre-implant suture initial modulus was compared to the rat skin initial modulus. Results of Brown-Forsythe and Welch ANOVA shown statistically significant differences between the pre implant PEUU cast wire, PPL, PGA and PDS groups versus the rat skin control group. Analysis showed no significant difference between PEUU ES wire and rat skin groups.

Figure 16B:
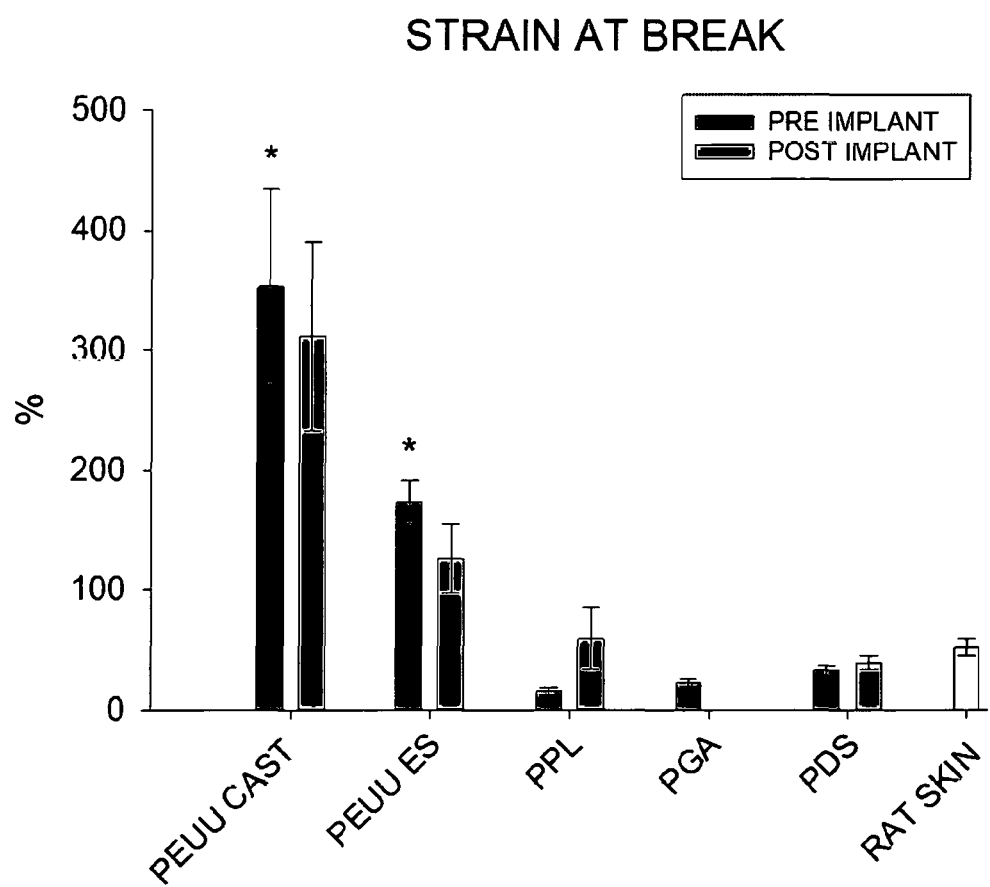

The results for the percent strain at break of the PEEU cast wire, PEUU ES wire, PPL, PGA, and PDS suture wires pre-implantation and post implantation can be found in FIG. 16B. Results of Brown-Forsythe and Welch ANOVA show statistically significant differences between the pre-implant PEUU cast and PEUU ES wire groups versus the rat skin control group.

Figure 16C:
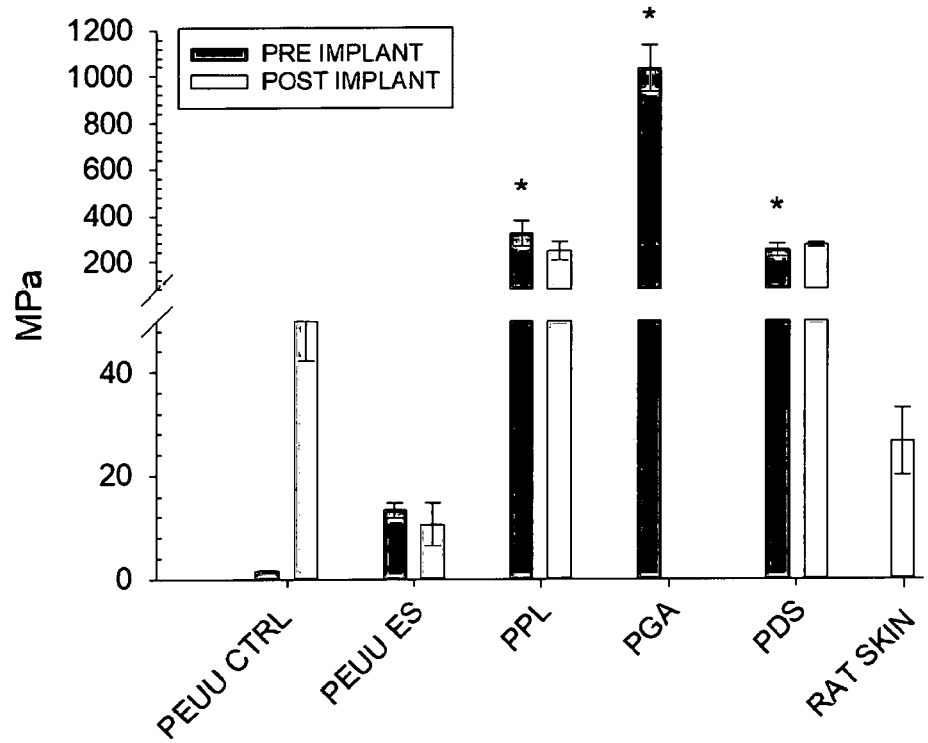

The results for the ultimate tensile strength of the PEEU cast wire, PEUU ES wire, PPL, PGA, and PDS sutures pre-implantation and post implantation can be found in FIG. 16C. Results of Brown-Forsythe and Welch ANOVA shown statistically significant differences between the pre-implant PPL, PGA, and PDS groups versus the rat skin control group. The analysis showed no significant difference between PEUU cast wire and PEUU ES wire and rat skin groups.

Figure 17:
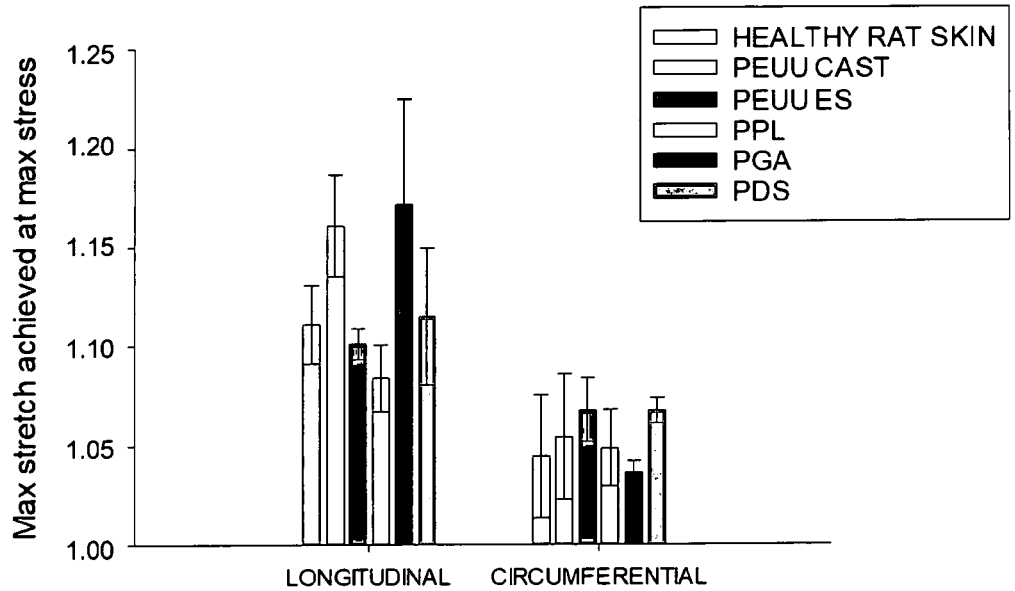
FIG. 17 is a graph depicting the biaxial mechanical test results for the scar area removed from a rat after 1 month of healing following suturing with PEUU cast wire, PEUU ES wire, PPL, PGA, and PDS, as compared to healthy rat skin.

Biaxial testing of scar area. The results for the max stretch achieved for the PEUU cast wire, PEUU ES wire, PPL, PGA, and PDS sutured scar area, as compared to healthy rat skin can be found in FIG. 17. The biaxial mechanical characterization showed no differences among the suture material groups.

We claim:

1. An apparatus for producing a fibrous thread or rope, comprising:
   a base comprising an electric lead;
   a first rotating head rotatably connected to the base and electrically-connected to the electric lead of the base, wherein the first rotating head rotates about an axis of rotation, the first rotating head comprising:
      a first fiber collection spool;
      a motor configured to rotate the first fiber collection spool;
      a first electrode having a distal end and a proximal end attached to the first fiber collection spool and electrically-connected to the electric lead; and
      a first guide at the axis of rotation of the first rotating head configured to rotatably-retain the first electrode and through which the distal end of the first electrode is extended or extendable on action of the first fiber collection spool;
   a second electrode having a distal end spaced apart from the distal end of the first electrode when the first electrode extends through the first guide and defining a gap between the first electrode and the second electrode, and connected at its proximal end to the electric lead or to a second electric lead; and
   a motor configured to rotate the first rotating head about the axis of rotation of the first rotating head.

2. The apparatus of claim 1, wherein the distal end of the second electrode is spaced from 1 to 10 inches from the distal end of the first electrode when the first electrode extends through the first guide.

3. The apparatus of claim 1, wherein the first electrode and/or second electrode are wire electrodes.

4. The apparatus of claim 1, further comprising:
   a second rotating head rotatably connected to the base and electrically-connected either to the electric lead of the base or to a second electric lead, wherein the second rotatable head rotates about an axis of rotation, the second rotating head comprising:
      a second fiber collection spool with a motor configured to rotate the second fiber collection spool;
      the second electrode having its proximal end attached to the second fiber collection spool; and
      a second guide at the axis of rotation of the second rotating head configured to rotatably-retain the second electrode and through which the distal end of the second electrode is extended or extendable on action of the second fiber collection spool; and
   a motor configured to rotate the second rotating head about the axis of rotation of the second rotating head.

5. The apparatus of claim 4, further comprising one or more controllers adapted to control the direction and velocity of the motors of the first rotating head and the first fiber collection spool, and when present the motors of the second rotating head and the second fiber collection spool, thereby controlling direction and velocity of rotation of the first rotating head and the first fiber collection spool, and when present, the direction and velocity of rotation of the second rotating head and the second fiber collection spool.

6. The apparatus of claim 4, wherein the distal end of the second electrode is extended or extendable on rotation of the second fiber collection spool.

7. The apparatus of claim 1, further comprising an electrospinning nozzle configured to deposit a polymer composition in the gap between the first electrode and the second electrode and connected to an electric lead,
   wherein the electrospinning nozzle is mounted on a movable stage,
   wherein the electrospinning nozzle is fluidly connected to a polymer reservoir to feed polymer through the electrospinning nozzle, and
   wherein a power source is connected to the electric lead of the electrospinning nozzle.

8. The apparatus of claim 7, further comprising an electrospray nozzle configured to deposit a liquid composition in the gap between the first electrode and the second electrode and connected to an electric lead,
   wherein the electrospray nozzle is mounted on a moveable stage,
   wherein the electrospray nozzle is fluidly connected to a liquid reservoir to feed liquid through the electrospinning nozzle, and
   wherein a power source is connected to the electric lead of the electrospray nozzle.

9. The apparatus of claim 8, wherein the controller, or one or more additional controllers, controls, when present, location of the electrospinning nozzle, flow rate of the polymer composition through the electrospinning nozzle, location of the electrospray nozzle, flow rate of the liquid through the electrospray nozzle, charge on the first and second electrodes, charge on the electrospinning nozzle, and/or charge on the electrospray nozzle.

10. The apparatus of claim 1, wherein the distal end of the first electrode is extended or extendable on rotation of the first fiber collection spool.

11. A method of making a continuous fiber thread or rope, comprising:
    initiating electrodeposition by feeding a polymer solution through an electrospray nozzle into a gap between a first electrode and a second electrode of an apparatus comprising:
       a base comprising an electric lead electrically-connected to a power source providing a voltage suitable for electrodeposition;
       a first rotating head rotatably connected to the base and electrically-connected to the electric lead of the base, wherein the first rotating head rotates about an axis of rotation, the first rotating head comprising:

a first fiber collection spool;

a motor configured to rotate the first fiber collection spool;

a first electrode having a distal end and a proximal end attached to the first fiber collection spool and electrically-connected to the electric lead; and a first guide at the axis of rotation of the first rotating head configured to rotatably-retain the first electrode and through which the distal end of the first electrode is extended or extendable on action of the first fiber collection spool, and wherein the distal end of the first electrode extends through the first guide;

a second electrode having a distal end spaced apart from the distal end of the first electrode and defining a gap between the first electrode and the second electrode, and connected at its proximal end to the electric lead or to a second electric lead connected to a power source providing a voltage;

a motor configured to rotate the first rotating head about the axis of rotation; and an electrospinning nozzle configured to deposit a polymer composition in the gap between the first electrode and the second electrode and electrically-connected to an electric lead and a power source providing a voltage to the electrospinning nozzle that produces an electrical field with the first and second electrode for electrodeposition of the polymer composition in the gap between the distal ends of the first electrode and second electrode, thereby forming nascent thread or rope, and attaching the nascent thread or rope to the first electrode and to the second electrode; and rotating the first fiber collection spool during electrodeposition of the polymer solution at a rate to first draw the first electrode, and then the nascent electrodeposited thread or rope connected to the distal end of the first electrode, through the first guide and onto the first fiber collection spool, such that polymer fibers are electrodeposited onto and between nascent thread or rope attached to the first electrode and the second electrode, thereby extending the length of the thread or rope and winding the nascent thread or rope about the first fiber collection spool.

12. The method of claim 11, further comprising electrospraying a liquid onto the fiber from an electrospray nozzle configured to deposit a liquid composition in the gap between the first electrode and the second electrode and connected to an electric lead and a power source providing a voltage suitable for electrospraying.

13. The method of claim 11, wherein the apparatus further comprises:

a second rotating head rotatably connected to the base and electrically-connected either to the electric lead of the base or to a second electric lead connected to a power supply providing a voltage suitable for electrodeposition, wherein the second rotatable head rotates about an axis of rotation, the second rotating head comprising:

a second fiber collection spool with a motor configured to rotate the second fiber collection spool;

the second electrode having a proximal end electrically connected to the electric lead of the base or to a second lead connected to a power supply and electrically-connected to the electric lead, and a distal end; and a second guide at the axis of rotation of the second rotating head configured to rotatably-retain the second electrode and through which the distal end of the second electrode is extended or extendable on rotation of the second fiber collection spool, and wherein the distal end of the first electrode extends through the second guide at least during initiation of electrodeposition; and a motor configured to rotate the second rotating head about the axis of rotation of the second rotating head.

14. The method of claim 13, further comprising, after rotating the first fiber collection spool during electrodeposition of the polymer solution, rotating the second fiber collection spool to draw the fiber away from the first fiber collection spool and through the second guide while electrodepositing an additional layer or a liquid on the thread or rope.

15. The method of claim 13, comprising rotating the first head and the second head synchronously to produce an untwisted thread or rope and/or an untwisted additional layer.

16. The method of claim 11, comprising rotating at least the first head to impart a twist in the thread or rope and/or in one or more additional layers.

17. The method of claim 11, wherein the distal end of the first electrode is extended or extendable on rotation of the first fiber collection spool.

* * * * *